US011931739B2

(12) United States Patent
Roussie et al.

(10) Patent No.: US 11,931,739 B2
(45) Date of Patent: Mar. 19, 2024

(54) DEVICES, METHODS, AND KITS FOR ISOLATION AND DETECTION OF ANALYTES USING MICROSLIT FILTERS

(71) Applicants: SiMPore Inc., West Henrietta, NY (US); University of Rochester, Rochester, NY (US)

(72) Inventors: James A. Roussie, Rochester, NY (US); James L. McGrath, Fairport, NY (US); Richard E. Waugh, Pittsford, NY (US); Kilean S. Lucas, Bozeman, MT (US); Joshua J. Miller, Rochester, NY (US)

(73) Assignees: SiMPore Inc., West Henrietta, NY (US); University of Rochester, Rochester, NY (US)

( * ) Notice: Subject to any disclaimer, the term of this patent is extended or adjusted under 35 U.S.C. 154(b) by 403 days.

(21) Appl. No.: 16/639,471

(22) PCT Filed: Aug. 16, 2018

(86) PCT No.: PCT/US2018/046817
§ 371 (c)(1),
(2) Date: Feb. 14, 2020

(87) PCT Pub. No.: WO2019/036545
PCT Pub. Date: Feb. 21, 2019

(65) Prior Publication Data
US 2021/0129146 A1    May 6, 2021

Related U.S. Application Data

(60) Provisional application No. 62/546,299, filed on Aug. 16, 2017.

(51) Int. Cl.
B01L 3/00        (2006.01)
G01N 1/40        (2006.01)
G01N 33/537      (2006.01)

(52) U.S. Cl.
CPC ...... B01L 3/502753 (2013.01); G01N 1/4077 (2013.01); G01N 33/537 (2013.01);
(Continued)

(58) Field of Classification Search
None
See application file for complete search history.

(56) References Cited

U.S. PATENT DOCUMENTS 5,919,364 A * 7/1999 Lebouitz ............ B01D 67/0093
                                                    210/500.25
9,089,819 B2   7/2015 Walavalkar et al.
(Continued)

OTHER PUBLICATIONS

Sajay, et al., "Microfluidic platform for negative enrichment of circulating tumor cells," Biomed Microdevices, DOI 10.1007/s10544-014-9856-2; Mar. 27, 2014, all enclosed pages cited.
(Continued)

Primary Examiner — Lore R Jarrett
(74) Attorney, Agent, or Firm — Hodgson Russ LLP

(57) ABSTRACT

Provided are methods, devices, and kits for the isolation and detection of one or more analytes of interest from a biological sample using microslit filter membranes. In various examples, the methods use capture particles and binding agents for specific recognition of one or more analytes of interest.

26 Claims, 18 Drawing Sheets

(52) U.S. Cl.
CPC .............. *B01L 2300/0681* (2013.01); *G01N 2001/4088* (2013.01)

(56) References Cited

U.S. PATENT DOCUMENTS

| | | | |
|---|---|---|---|
| 9,599,610 B2 | 3/2017 | Sitdikov et al. | |
| 2006/0278580 A1* | 12/2006 | Striemer | H01M 8/1037 |
| | | | 216/2 |
| 2009/0131858 A1 | 5/2009 | Fissell et al. | |
| 2012/0171087 A1* | 7/2012 | Gaborski | B01L 3/5021 |
| | | | 210/500.21 |
| 2016/0199787 A1* | 7/2016 | Striemer | B01D 67/0037 |
| | | | 216/56 |
| 2018/0029033 A1* | 2/2018 | Koser | G01N 35/1097 |

OTHER PUBLICATIONS

Striemer, et al., "Charge- and size-based separation of macromolecules using ultrathin silicon membranes," Nature, vol. 445, Feb. 15, 2007, all enclosed pages cited.

Qi, et al., "Highly Porous Silicon Membranes Fabricated from Silicon Nitride/Silicon Stacks," Small 10, No. 14, 2014, all enclosed pages cited.

* cited by examiner

Neat Urine

1 μm FTV

DEVICES, METHODS, AND KITS FOR ISOLATION AND DETECTION OF ANALYTES USING MICROSLIT FILTERS

CROSS REFERENCE TO RELATED APPLICATIONS

This application claims priority to U.S. Provisional Application No. 62/546,299, filed on Aug. 16, 2017, the disclosure of which is hereby incorporated by reference.

STATEMENT REGARDING FEDERALLY SPONSORED RESEARCH

This invention was made with government support under contract no. GM116190-01A1 awarded by the National Institutes of Health. The government has certain rights in the invention.

FIELD OF THE DISCLOSURE

This disclosure relates to the capture and isolation of analytes of interest from a biological sample for purposes of performing analyses on the analytes, and more particularly, the capture of such analytes within complexes that can be efficiently isolated from undesired species using microslit filters with high permeation capacity and precision molecular cut-off characteristics.

BACKGROUND OF THE DISCLOSURE

Efficient isolation of desired species of interest from biological samples is a critical step required for research and clinical analytical purposes. While many filtration-based methods have been developed for these purposes, these methods are generally low yielding when offering high purity or are generally high yielding when offering low purity.

This compromise between yield and purity is a consequence of several interacting factors, including the high abundance of cellular and molecular species (i.e., concentration) of the species within biological samples, in relation to the permeation resistance and the aspect ratio of through-holes (i.e., openings) in typical polymeric filter membranes. For example, filtration of desired solutes (e.g., capture particles that are added to a biological sample for selective binding of a species of interest) from undesired solutes of a biological sample (e.g., high abundant hemocytes of a whole blood sample) is practically difficult using typical polymeric filters with either cylindrical pore or tortuous path openings. However, such a filtration would be more easily performed using filters with straight-through, cubic prism-like (e.g., rectangular prism) openings rather than cylindrical pore or tortuous path openings. In the above example, for instance, the selective binding capture particles could be more readily resolved from the highly abundant hemocytes using a filter with cubic prism (e.g., rectangular prism) openings.

The cylindrical pores and/or tortuous paths of typical polymeric filter membranes are also generally overwhelmed by the high abundance of solutes in biological samples due to their high permeation resistance that is a consequence of their thickness, aspect ratio of cylindrical pores, and/or there internal surface area along tortuous paths. Thus, these membranes lack sufficient capacity to permeate highly abundant, undesired solutes, while simultaneously retaining desired solutes (and any related species of interest).

The high permeation resistance of typical polymer filter membranes also generally requires that most isolations of a species of interest from biological samples are performed with high pressure conditions for effectiveness. Not only does high pressure tend to cause filter fouling (limiting permeation of undesired solutes), it also can cause unwanted effects, such as cell lysis or protein denaturation and/or aggregation. For instance, if the species of interest is a cell-free DNA or RNA species that is to be isolated from whole blood and then subsequently analyzed by a sequencing or an amplification reaction, then cell lysis could contaminate the preparation with undesired genomic and/or cytoplasmic nucleic acids, leading to spurious sequencing data.

What is needed for high yield and high purity isolation of desirable solutes from biological samples for analytical purposes is a method that can isolate and capture desired solutes (and related species of interest) that functions in combination with a fluidic device integrating an ideal membrane filter of appropriate thinness, thus possessing low permeation resistance and high permeation capacity, which can operate under low pressure conditions, with opening aspect ratios (i.e., cubic prism or rectangular prism openings) that reduce fouling behavior and allow efficient removal of undesired solutes, while retaining the captured, desired solutes (and related species of interest).

The previously described method and fluidic device integrating an ideal membrane filter of desired thinness, opening aspect ratio, and low pressure operation, could also provide a number of hydrodynamic characteristics that are advantageous over well-known analyte isolation methods and devices which rely upon magnetic properties of capture particles alone (e.g., Sitdikov et al., US2014/0170652). For example, size selective analyte isolation using ideal membrane filters offers the potential for isolation of multiple analytes from one biological sample(using different sized capture particles for each analyte) and multiple membrane filters with openings corresponding in size to each capture particles' size. Such multiple analyte isolations from one sample is not achievable with magnetic particle-based separations.

SUMMARY OF THE DISCLOSURE

The present disclosure provides methods for the isolation of one or more species of interest (e.g., an analyte of interest) from a biological sample for analytical purposes. The one or more methods are based on formation of analyte-affinity moiety-capture particle complexes and use of microslit filters of the present disclosure.

In an aspect, a method of the present disclosure comprises, optionally, forming analyte-affinity moiety-capture particle complexes, filtering the sample to isolate and retain the desired solutes (e.g., the analyte-affinity moiety-capture particle complexes), while removing or permeating undesired solutes (e.g., undesired biological sample constituents), optionally, eluting the complexes and/or disassociating the complexes to liberate their species, and, optionally, carrying out one or more analytical assays on such complexes and species. The filtration that isolates and retains desired analyte-affinity moiety-capture particle complexes from undesired solutes can make use of a filtration membrane of specified characteristics. This filtration membrane can be referred to as a microslit filter or as microslit filters.

In an aspect, the present disclosure further provides a method for a direct assay to determine the presence or absence of at least one analyte of interest within a biological sample, by recording the optical diffraction spectra of microslit filters after the filtration step to observe any potentially isolated complexes as indicative of the at least one analyte's presence.

In an aspect, the present disclosure provides fluidic devices for carrying out the methods of the disclosure. In various examples, these fluidic devices include one or more microslit filters for isolating analyte-affinity moiety-complexes and/or sample preparation, as well as one or more additional sorting membranes for resolving distinct sets of such complexes into separate fractions. In an example, the fluidic device comprises at least one microslit filter. In an another example, the fluidic device comprises at least one microslit filter and at least one sorting membrane In a further aspect, the thickness, porosity, and opening aspect ratio of microslit filters are specified in examples disclosed herein, such that the thickness and porosity properties promote low species permeation resistance and high permeability (i.e., high permeation capacity, low pressure operation), while the opening aspect ratio promotes non-fouling behavior and precision molecular cut-off (i.e., isolation and retention of desired complexes and removal of undesired species, complexes, and non-complexed species). In further examples, the characteristics of microslit filters are specified for performing an upstream sample preparation as disclosed herein.

In a further aspect, the characteristics of capture particles are specified by examples disclosed herein, such that the capture particles allow retention and isolation of formed analyte-affinity moiety-capture particle complexes and the permeation of undesired species and complexes, as well as removal of non-complexed components. In these examples, the diameter of the capture particles are specified with respect to width and aspect ratio of the openings of the microslit filters, or with respect to the openings of sorting membranes, that will be used in conjunction with the capture particles to affect the desired filtration outcome. Furthermore, one or more physical properties of the capture particles are specified in combination with its diameter to provide a means of identifying a distinct set of a plurality of capture particles.

In an aspect, the present disclosure provides a kit comprising specified devices and reagents for carrying out the methods of the disclosure. Since the physical properties of microslit filters (e.g., thickness, porosity and opening aspect ratio and size) should be specified relative to capture particle size, and since microslit filter physical properties should be further specified for efficient processing of highly abundant species of biological samples, the devices and reagents of the disclosed kit are intended to be used as a combined system. Accordingly, in an aspect, a kit of the present disclosure comprises: a fluidic device, a plurality of capture particles, affinity moieties that bind one or more analytes, and affinity moieties that bind the analyte-binding affinity moieties.

BRIEF DESCRIPTION OF THE FIGURES

For a fuller understanding of the nature and objects of the disclosure, reference should be made to the following detailed description taken in conjunction with the accompanying figures.

DETAILED DESCRIPTION OF THE DISCLOSURE

Figure 1:
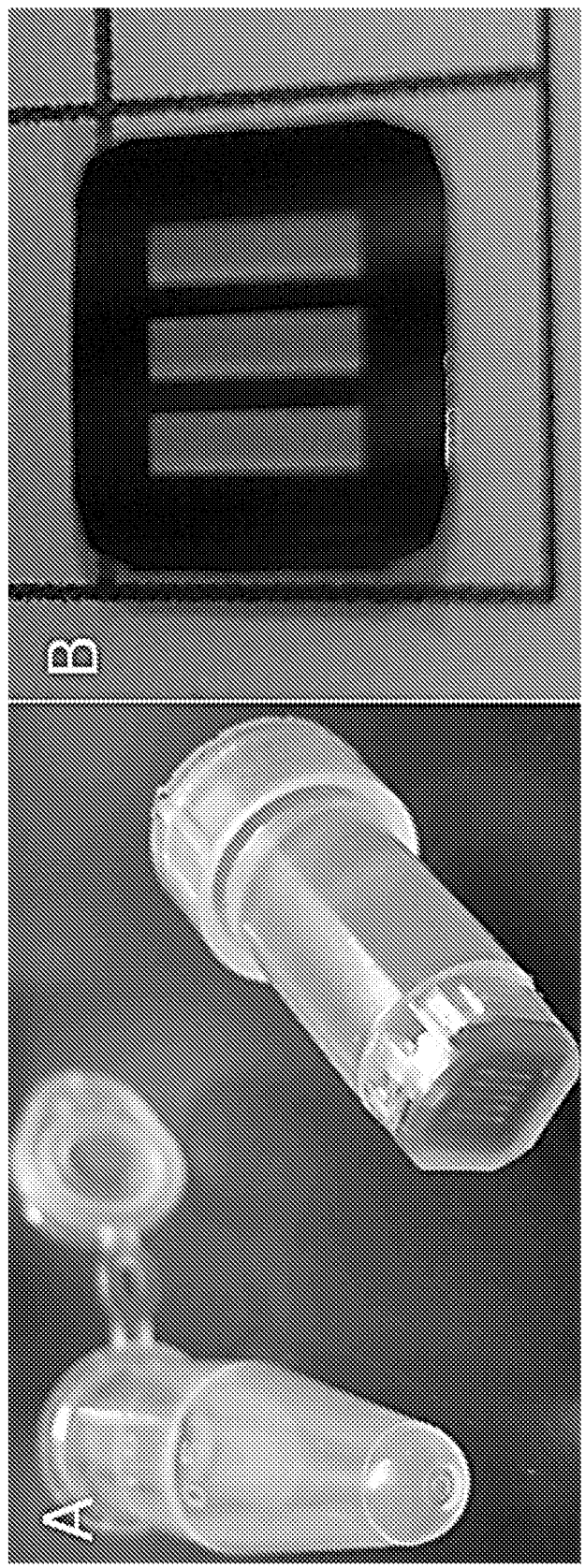
FIG. 1 provides images of a representative microslit filter and a representative fluidic device incorporating such a microslit filter. (A) shows a representative fluidic device incorporating a microslit filter, wherein the microslit filter is integrated into a centrifuge tube insert fluidic device for dead-end (normal) flow filtration purposes. (B) shows a representative microslit filter comprising 400 nm thick silicon nitride membranes, with three 0.7×3 mm suspended membranes, disposed on a silicon substrate of 5.4×5.4 mm and 0.3 mm thickness.

Although claimed subject matter will be described in terms of certain embodiments and examples, other embodiments and examples, including embodiments and examples that do not provide all of the benefits and features set forth herein, are also within the scope of this disclosure. Various structural, logical, and process step changes may be made without departing from the scope of the disclosure.

Ranges of values are disclosed herein. The ranges set out a lower limit value and an upper limit value. Unless otherwise stated, the ranges include all values to the magnitude of the smallest value (either lower limit value or upper limit value) and ranges between the values of the stated range.

The present disclosure provides methods for the isolation of one or more species of interest (e.g., an analyte of interest) from a biological sample for analytical purposes. The one or more methods are based on formation of analyte-affinity moiety-capture particle complexes and use of microslit filters of the present disclosure.

In an aspect, a method of the present disclosure comprises, optionally, forming analyte-affinity moiety-capture particle complexes, filtering the sample to isolate and retain the desired solutes (e.g., the analyte-affinity moiety-capture particle complexes), while removing or permeating undesired solutes (e.g., undesired biological sample constituents), optionally, eluting the complexes and/or disassociating the complexes to liberate their species, and, optionally, carrying out one or more analytical assays on such complexes and species. The filtration that isolates and retains desired analyte-affinity moiety-capture particle complexes from undesired solutes can make use of a filtration membrane of specified characteristics. This filtration membrane can be referred to as a microslit filter or as microslit filters.

In an example, a method for capturing and isolating an analyte of interest from a biological sample (e.g., biofluid) comprises:

(a) optionally, adding a first binding agent to the biological sample (e.g., biofluid) such that a first ligand on the analyte of interest is bound by the first binding agent, forming a first biological sample (e.g., biofluid) comprising an analyte-first binding agent complex;

(b) optionally, adding capture particles to the mixture of biological sample (e.g., biofluid) and first binding agent, such that the first binding agent is bound by the capture particles, and a second biological sample (e.g., biofluid) comprising an analyte-first binding agent-capture particle complex is further formed;

(c) contacting the biofluid-complex mixture (e.g., the second biological sample (e.g., biofluid)) with a microslit filter, such that the analyte-first binding agent-capture particle complex is retained by the microslit filter and undesired solutes permeate through the microslit filter;

(d) optionally, removing (e.g., by eluting or disassociating) the retained analyte-first binding agent-capture particle complex from the microslit filter; and (e) optionally, performing one or more assays on the species of the isolated and eluted analyte-first binding agent-capture particle complexes.

Analytes of interest include, but are not limited to, species such as intact cells, sub cellular components (e.g., vesicles or organelles), proteins, nucleic acids, carbohydrates, lipids, peptides, viruses, bacteria, fungi, drugs, metabolites or other low molecular mass species, and the like, and any combinations thereof.

The biological sample bearing the analytes of interest may be a biofluid, which may include, for example, cell lysates, venous or arterial whole blood, plasma, serum, sputum, urine, cerebrospinal fluid, conditioned cell culture media or other fluids derived from cell culture and other fluids containing molecules of biological origin, or any solutions in contact with biological tissues (e.g., bodily secretions, discharges, and/or excretions, as well as swabs and/or aspirates of bodily tissues, and the like), among others. In some examples, an optional pretreatment (e.g., sample pretreatment) of the biofluid sample is carried out prior to carrying out the methods of the present invention, such as, for example, low-speed centrifugation of whole blood to remove hemocytes (thus forming a plasma sample), lysis of a population of cells (thus forming a cell lysate), or fluidization of a solid sample (thus forming a liquid sample) among many other possible pretreatment alternatives. In other examples, sample pretreatment comprises filtration through a microslit filter to retain certain species, while permeating other species. For purposes of this disclosure, such a sample pretreatment may be referred to as an upstream sample preparation.

In addition to biological samples, non-biological samples that are compatible with the present invention could include, but are not limited to, samples of water, industrial discharges, food products, milk, air filtrates, among others, and thus include food, environmental and industrial samples and the like.

An affinity moiety (e.g., the first binding agent of (a)) binds a first ligand of the analyte, such that an analyte-first binding agent complex is formed. Non-limiting examples of first binding agent are be chosen from among classes of affinity moieties that include monoclonal or polyclonal antibodies or fragments derived from such antibodies, DNA or RNA oligonucleotides or aptamers, peptides or modified peptide derivatives, lectins, bacteriophages, small molecules, proteins or their domains with known protein or nucleic acid binding capacity, and the like.

For purposes of this disclosure, an affinity moiety possesses specific molecular interaction capacity, with a relatively high association rate and low disassociation rate for its cognate target binding molecule or ligand (e.g., analyte). It is generally recognized that for practical purposes, an affinity moiety's relatively high association rate and low disassociation rate for its ligand should result in the affinity moiety possessing an equilibrium disassociation constant ($K_d$) that is within the range of pM to nM values. The three-dimensional structure of the affinity moiety is such that it forms high-affinity interactions upon binding of its ligand through, for example, hydrophobic, ionic, van der Waals, or hydrogen-bonding interactions, and the like. For example, the three-dimensional structure of monoclonal, polyclonal or antibody fragments is determined by the amino acid sequence of these proteins, and more particularly, the specific and unique amino acid sequences of the $F_v$ or $F_{AB}$ regions of such proteins determines its affinity for the epitopes of a ligand. As another example, the three-dimensional structure of lectins, and in particular, the specific and unique amino acid sequence of its carbohydrate-binding region determines its affinity for carbohydrate structures of its ligands. As an additional example, the three-dimensional structure of an aptamer is determined by its nucleic acid sequence, such that the resulting three-dimensional structure of the aptamer forms high-affinity binding interactions sites with regions of its ligands. As another example, the nucleic acid sequence of an oligonucleotide determines its sequence-specific binding to complementary nucleic acid sequences through canonical base-pairing interactions. Of course, many other possible affinity moiety structural interactions with target ligands are possible and the examples have been provided for exemplary purposes only. In the various embodiments disclosed herein, these exemplary interactions (as well as other possible interactions) describe the manner in which first binding agents interact with target analytes and describe the manner in which first binding agents interact with any second binding agents, as well as any further sets of interactions between analytes and/or binding agents.

For purposes of this disclosure, it is understood that a plurality of first binding agent molecules are used in the methods disclosed herein and that this plurality may be referred to as a first binding agent or as first binding agents. In some examples, the first binding agent is added to the biofluid prior to adding subsequent capture particles to avoid potential steric or other physical constraints that may potentially limit interactions between the first binding agents and their cognate analyte species. A period of time for incubation of the first binding agent with the biofluid may be used to promote complex formation. In an example, the incubation conditions is specified to promote the strength of the initial analyte-first binding agent interaction, if desired; the incubation temperature or the salt concentration and/or pH of the incubation solution is specified to promote these interactions.

In various examples, the first binding agent is monovalent or multivalent. A monovalent first binding agent can bind one first ligand of one analyte, a multivalent first binding agent can bind two or more first ligands of one analyte, or a multivalent first binding agent can bind one first ligand of one analyte and a different first ligand of another analyte. In other examples, two or more monovalent first binding agents bind the same first ligand on an analyte (i.e., competitive binding) or two or more monovalent first binding agents bind two or more first ligands of two or more different analytes. In examples using two or more multivalent first binding agents, multiple first ligands of two or more analytes are bound in a variety of combinations. In some examples, the first binding agents are of the same class of affinity moiety, while in other examples, the first binding agents are a mixture of different classes of affinity moieties. An exemplary monovalent binding agent could be a monoclonal antibody, while an exemplary multivalent binding agent is a polyclonal antibody. For purposes of this disclosure, a ligand represents a portion of an analyte with which the binding agent interacts. For example, a first ligand could be the epitope of an analyte bound by a monoclonal antibody or the epitopes of an analyte bound by a polyclonal antibody.

The addition of capture particles (e.g., of (b)) comprises the addition of a plurality of capture particles to the biofluid-first binding agent complex mixture, wherein this plurality of capture particles binds the complexes, further forming a analyte-first binding agent-capture particle complex. In some examples, the plurality of particles binds a first binding agent. In other examples, a set of the plurality of particles binds one first binding agent, while a different set of the plurality of particles binds a different first binding agent. In further examples, a set of the plurality of particles binds different first binding agents targeting different first ligands of one analyte, while a different set of the plurality of particles binds different first binding agents targeting different first ligands of another analyte.

In an example, capture particles are functionalized with a second binding agent (e.g., affinity moieties) of their own (e.g., in order to capture the first binding agent). The second binding agents are appropriate for the nature and composition of the first binding agent and can be chosen from the affinity moieties listed for first binding agents. As examples, the particles can be functionalized with: 1) secondary antibodies or S. aureus protein A or protein G to capture antibodies: 2) avidin or streptavidin to capture biotinylated antibodies; or 3) complimentary sequence oligomers or poly-amines (e.g., imidazole or lysine) to capture DNA or RNA aptamers.

In some examples, the first binding agent are directly coupled to the plurality of capture particles through, for example, covalent attachment or by absorption. In other examples, two or more first binding agents are directly coupled to a set of the plurality of particles. In examples wherein the first binding agent is directly coupled to the particles (e.g., in a) and b)) the method would be performed simultaneously as one active step, and a second binding agent of the capture particles would be omitted. Exemplary means for covalent attachment of binding agents to capture particles could include, but are not limited to, linker chemistries such as silane, amino, carboxyl, thiol/sulfhydryl, isothiocyanate, epoxide, alkane, mercaptan, hydrazine, N-glycan, or O-glycan, among other possibilities. Exemplary means for absorbing binding agents to capture particles could include, but are not limited to, interactions such as hydrophobic, hydrophilic, physabsoprtion, ionic, van der Waals, or hydrogen-bonding, among others.

The capture particles can be of organic, inorganic, or combined composition (e.g., silica, agarose, latex, polystyrene, iron oxide, cadmium selenide, and the like). In examples where different sets of the plurality of particles are used, the physical properties of the sets of particles are specified to provide a means for identifying a particular set of particles. For example, the diameter and/or fluorescent absorbance and emission spectrum of a set of particles is made distinct from other sets of particles to endow each set of particles with its own unique optical signals that can be detected by a variety of optical modalities. However, the composition of capture particles should be chosen as to avoid spurious effects that may otherwise complicate the identification of distinct sets of capture particles or any downstream analytical assays (e.g., autofluorescence of some polymeric particles). If the composition of the capture particles endows them with ferromagnetic or paramagnetic properties, such properties are incidental and not relevant to the methods of the present disclosure (i.e., capture particle magnetic properties are not exploited as a means for their isolation). In an example, the diameter of an incidentally magnetic capture particle, with respect to the openings of a microslit filter of the present invention, is used to isolate the capture particle and any of the particle's associated complexes. In this example, the incidental magnetic property of the capture particle (and any associated complexes) is not used for its isolation.

The filtration (e.g., of (c)) can be performed by contacting the mixture of biofluid and analyte-first binding agent-capture particle complex with a microslit filter of specified characteristics. For example, the width of the microslit filter's openings can be specified to retain a set of the complexes, to permeate other sets of complexes, and to permeate free, non-complexed species. The diameter of capture particles must be specified with respect to the width of the microslit filter's openings in order to affect the desired retention or permeation outcomes.

To retain complexes, either the capture particles' diameter must be greater than the width of the microslit filter's openings, or if the capture particles' diameter is less than the width of the microslit filter's openings, the chosen first binding agent(s) must promote the aggregation of multiple capture particles within complexes so that their aggregated diameter exceeds the microslit filter's largest opening dimension. In these examples, it is recognized that retention of the particles and their associated species is desired as an isolation for subsequent use and analysis of complex-derived species, and that free, non-complexed species permeate through the microslit filter to remove these unwanted biofluid constituents. In examples where the particles permeate through the microslit filter, the particles' diameter must be less than the width of the microslit filter openings. In these examples, it is recognized that permeation of the particles and their associated complexes may be desired for a negative selection of unwanted biofluid constituents. However, where complexed species permeation is desired for concurrent negative selections, the capture particle's diameter, the nature of the first binding agent, and the amount of added negative selection capture particles should be carefully specified so as to avoid aggregation which would otherwise increase the diameter of complexes and lead to their potential retention. For example, the analyte may be a specific circulating cell type found in whole blood, whose native diameter is less than that of a microslit filter with opening widths that permit permeation of hemocytes as well as the circulating cell of interest; thus, these cells are able to permeate such a microslit filter. Upon addition of appropriate capture particles and first binding agent(that can selectively bind the circulating cell of interest) to the whole blood sample, the resultant diameter of the circulating cell of interest-first binding agent-capture particle complexes exceeds the specified opening widths of the microslit filter; thus, the cell of interest is selectively retained and the hemocytes are removed. Of course, other possibilities exist and this example is provided for exemplary purposes only.

The filtration (e.g., of (c)) can be performed by several flow modalities. For example, the filtration comprises dead-end or normal flow initiated by gravity, hydrostatic pressure, pumping, vacuum, centrifugation, or gas pressurization, where the biofluid-complex mixture is introduced to the cis-side of the microslit filter and translocates to the opposing trans-side of the microslit filter. In another example, the filtration comprises tangential flow initiated by bulk flow of biofluid-complex mixture and buffer, respectively, on opposing cis and trans-sides of the microslit filter.

The filtration (e.g., of (c)) can be performed at a range of pressurization that is compatible with maintaining the integrity of cellular and molecular constituents of the biofluid sample. For instance, the pressurization can be from 10 Pa to 1.0 kPa and all Pa values therebetween. In another example, the pressurization can be that only applied by hydrostatic pressure. The pressurization can be sufficiently low that the shear forces applied to cells when permeating the microslit filters do not cause cell lysis. For example, a microslit filter of 8×50 µm openings and 400 nm thickness applies a maximum of 18 dynes/cm$^2$ at 1.0 kPa, while 1,500 dynes/cm$^2$ is known, for example, to cause red blood cell lysis (Leverett et al, 1972).

In some examples, one or more washing steps follow (c) in order to remove nonspecifically bound contaminants associated with the retained complexes. For example, the wash solution is any buffer compatible with biological specimens. The wash solution includes, for example, ionic or non-ionic detergents or has a specified salt concentration or pH to promote removal of non-specifically bound contaminants. Similar flow modalities as described for the filtration of c) could be used for any washing steps. Any such washing steps, if included, can remove soluble proteins and/or other matrix interferents from any retained complexes, and such soluble proteins and/or matrix interferents transferred to a waste vessel or fluidic chamber.

The optional elution or disassociation (e.g., of (d)) can be performed by either eluting intact complexes or by disassociating the complexes to liberate their species. Following (d), intact complexes and/or any of their derived species can be transferred to another appropriate receptacle (e.g., vessel, surface, or instrument, and the like) for subsequent analytical assays (e.g., of (e)). Step (d) would follow any washing step, if applied. For example, elution of intact complexes could be performed by introducing a bolus of buffer solution to flush any retained complexes from the microslit filter by reversing any of the flow modalities used for initial retention of such complexes (e.g., during (c)). As further examples, complexes could be disassociated by specifying salt and/or pH conditions to disrupt analyte-binding agent interactions, by adding a molecular excess of a competitively binding ligand to dissociate analytes from binding agents, by disrupting complexes by heat denaturation or sonication, or breaking covalent bonds by photolysis or with a chemical reagent to disrupt complexes. Of course, other possibilities exist and these examples are merely listed for exemplary purposes.

The one or more analytical assays (e.g., of (e)) can be performed on eluted complexes and/or their derived species to identify and quantify the presence or absence of any analyte(s) of interest. As examples, these assays could include a sequencing reaction, an amplification reaction, polymerase chain reaction, reverse transcriptase-polymerase chain reaction, ligase chain reaction, Northern blotting, Southern blotting, fluorescent hybridization, enzymatic treatment, labeling with second binding agents, enzyme-linked immunosorbent assay, Western blotting, immunoprecipitation, fluorescence-activated sorting, optical imaging, electron microscopy, surface plasmon resonance, Raman spectroscopy, or interferometry, among other possibilities. In some examples, the assay can be nanopore-based resistive pulse sensing; for example, as disclosed in Huff et al. (WO2016161402A1). In other examples, the assay can be arrayed imaging reflectometry (for example, as disclosed in Miller and Rothberg, U.S. Pat. No. 7,292,349). If multiple, first binding agents are used to capture two or more analytes, then assays for multiplex detection could be used to distinguish, identify and quantify multiple analytes. Of course, other assay possibilities exist and these examples are merely provided for exemplary purposes.

In an example of the method, the identification and/or quantification of analytes of interest can be performed using surrogate chemical tags particular to distinct analytes as disclosed in Huff et al. (WO2016161402A1); the disclosure of which is hereby incorporated by way of reference. For instance, an analyte is captured and isolated as above. However, as disclosed in Huff et al., the capture particles in this instance are labeled with one or more of a thermally, chemically, or photolytically liable chemical tag, and the appropriate means is used to release one or more of these liable tags from the capture particle while the analyte-first binding agent-capture particle complexes remain intact on the microslit filter surface. Subsequently, the chemical tag is analyzed by nanopore-based resistive pulse sensing, as measured by the translocation events of released tags passing through nanopores, in order to identify and/or quantify its surrogate analyte.

In another example, the first binding agent is a DNA or RNA aptamer that is directly coupled to the capture particle, wherein the coupling comprises a liable linker between the capture particle and a DNA or RNA aptamer. After formation of a analyte-first binding agent-capture particle complex and its subsequent isolation by the methods disclosed herein, the analyte-first binding agent complex (i.e., analyte-aptamer complex) could be liberated by chemical, mechanical, or photolytic methods, and the analyte-DNA or RNA aptamer complex assayed by nanopore-based resistive pulse sensing. In this example, the DNA or RNA aptamer alone (i.e., not bound to analyte) would be used as a reference; i.e., nanopore-based resistive pulse sensing is used to detect an increase in the molecular mass of translocating analyte-aptamer complexes in comparison to translocating aptamers alone in order to detect the presence of the analyte bound to the aptamer. For example, the first binding agent is a DNA aptamer that is covalently bound to 10 μm diameter capture particles via a thiol linkage, where the DNA aptamer binds an analyte of interest. Upon incubation of the aptamer-capture particles with a biofluid and the subsequent isolation of any analyte-aptamer-capture particle complexes by 8 μm width microslit filters, any analyte-aptamer complexes are liberated by a thiol reducing compound (e.g., 2-mercaptoethanol or dithiothreitol), and the liberated aptamers (and any associated analyte) are assayed by nanopore-based resistive pulse sensing.

In another example of the method, the optional elution or disassociation (e.g., of (d)) is omitted, such that the retained complexes remain on the microslit filter, and the one or more analytical assays (e.g., of (e)) are subsequently carried out on the complexes remaining on the microslit filter. In an additional example, complexes are labeled with a third binding agent bearing an enzyme, fluorophore, or quantum dot for purposes of generating an optical signal that can be detected by a variety of optical modalities. Those skilled in the art will appreciate this example is analogous to (in varying degree and extent) a sandwich immunosorbent assay. The third binding agent is chosen from any of the affinity moieties listed herein and should be specified so that it bind second ligands on their respective analytes and avoids competitive binding with the first ligands bound by the first binding agents. Of course, a variety of means of labeling and detection can be used and the example provided is merely for exemplary purposes.

In an aspect, a method of the disclosure further comprises, optionally, forming two or more distinct sets of analyte-affinity moiety-complexes, isolating these complexes with a microslit filter, eluting these complexes, and sorting the two or more sets of complexes into distinct populations for purposes of carrying out analytical assays on the species of the complexes. The sorting of two or more sets of complexes into distinct populations makes use of two or more sorting membranes.

In an example, a method for capturing and isolating two or more analytes of interest from a biological sample (e.g., biofluid) further comprises comprises:
(f) adding two or more distinct first binding agents targeting two or more distinct analytes to the biological sample (e.g., biofluid) such that at least one first ligand on the first analyte is bound by one first binding agent and a first ligand on a second analyte is bound by another first binding agent, forming at least two or more distinct analyte-first binding agent complexes;

(g) adding at least two or more sets of a plurality of capture particles to the mixture of the biological sample (e.g., biofluid) and first binding agents, such that one first binding agent is bound by one set of capture particles and subsequent first binding agents are bound by additional sets of capture particles, and at least two or more distinct analyte-first binding agent-capture particle complexes are further formed;

(h) contacting the biological sample (e.g., biofluid)-complex mixture with a microslit filter, such that the two or more analyte-first binding agent-capture particle complexes are retained by the microslit filter and undesired species and complexes permeate through the microslit filter;

(i) eluting the retained two or more analyte-first binding agent-capture particle complexes from the microslit filter;

(j) contacting the eluted two or more analyte-first binding agent-capture particle complexes with two or more sorting membranes, such that the two or more analyte-first binding agent-capture particle complexes are sorted into their respective, distinct populations;

(k) optionally, eluting or disassociating the sorted two or more analyte-first binding agent-capture particle complexes from the sorting membranes; and (l) optionally, performing one or more assays on the species of each distinct analyte-first binding agent-capture particle complexes.

In an example, a method for capturing and isolating two or more analytes of interest from a biological sample (e.g., biofluid) further comprises an upstream sample preparation step and further comprises (e.g., in addition to steps (f) through (l)):

(m) contacting the biological sample (e.g., biofluid) with a microslit filter, such that the undesired species are retained by the microslit filter and desired species permeate through the microslit filter;

(n) adding two or more distinct first binding agents targeting two or more distinct analytes to the microslit-filtered biological sample (e.g., biofluid) such that at least one first ligand on the first analyte is bound by one first binding agent and a first ligand on a second analyte is bound by another first binding agent, forming at least two or more distinct analyte-first binding agent complexes;

(o) adding at least two or more sets of a plurality of capture particles to the mixture of the biological sample (e.g., biofluid) and first binding agents, such that one first binding agent is bound by one set of capture particles and subsequent first binding agents are bound by additional sets of capture particles, and at least two or more distinct analyte-first binding agent-capture particle complexes are further formed;

(p) contacting the two or more analyte-first binding agent-capture particle complexes with two or more sorting membranes, such that the two or more analyte-first binding agent-capture particle complexes are sorted into their respective, distinct populations;

(q) optionally, eluting or disassociating the sorted two or more analyte-first binding agent-capture particle complexes from the sorting membranes; and (r) optionally, performing one or more assays on the species of each distinct analyte-first binding agent-capture particle complexes.

As further alternatives to the two preceding examples of further methods, the further methods can alternatively comprise capturing and isolating only one analyte of interest, rather than two or more such analytes, from a biological sample (e.g., biofluid). In examples where only one analyte is of interest, then only one first binding agent, one set of a plurality of capture particles, one microslit filter, and one sorting membrane is used.

In an example, sorting (e.g., of (j) and/or (p)), where the one or more are sorted into one or more distinct populations, is performed based on the physical properties of the sets of capture particles with respect to the filtration properties of the one or more sorting membranes. For example, a first sorting membrane having either cubic prism, rectangular prism, or cylindrical pore openings, corresponding in width or diameter, respectively, to the diameter of a first set of capture particles, is used to sort complexes born by this first set of capture particles. A second sorting membrane having either cubic prism, rectangular prism, or cylindrical pore openings, corresponding in width or diameter, respectively, to the diameter of a second set of capture particles, is used to sort complexes born by this second set of capture particles. Any third and successive sets of capture particles and their associated complexes is sorted by additional sorting membranes with openings corresponding to the diameter of capture particles of any third or successive sets. Of course, sorting membrane opening size and capture particle diameter are two of several possibilities and are merely listed for exemplary purposes.

The upstream sample preparation (e.g., the filtration of (m)) can be performed by contacting the biofluid with a microslit filter of specified characteristics. For example, the width of the microslit filter's openings can be specified to retain undesired species (e.g., cells or protein aggregates) to permeate other complexes, and to permeate free, non-complexed species. For example, a microslit filter having either cubic prism or rectangular prism openings, corresponding in width to the diameter of cells (e.g., hemocytes of blood or urothelia of urine) or protein aggregates (e.g., Tamm-Horsfall protein filaments of urine), could be used to retain these undesired species, while also permeating free, non-complexed species (e.g., analytes of interest). Of course, microslit width opening size is one of several possibilities and is merely listed for exemplary purposes.

In an example, filtration (e.g., of (h) and/or (m)) and the sorting (e.g., of (j) and/or (p)) can be performed using any of the previously described flow modalities for the filtration of (c). One or more optional washing steps to remove non-specifically bound contaminants is used (e.g., follows (h), (j), (m) and/or (p)), if desired, and use any of the previously described flow modalities for such washing steps. Any such washing steps, if included, may remove soluble proteins and/or other matrix interferents from any analyte-first binding agent-capture particle complexes retained on the sorting membranes, and such soluble proteins and/or matrix interferents transferred to a waste vessel or fluidic chamber. The elution (e.g., of (i), (k) and/or (q)) can similarly use any of the previously described flow modalities for the elution (e.g., of (d)).

In an example, where the multiple first binding agents are directly coupled to the sets of capture particles (e.g., (f) and (g); (n) and/or (o)) of these further methods is performed simultaneously as one active step (e.g., (g) and/or (o) would be omitted).

In an example, any of the optional methods described above for disassociating complexes are applied prior to (k) or (q), while the complexes remain on their respective sorting membranes, as an alternative to eluting intact complexes in (k) or (q). The species derived from these dissociated complexes are further subjected to any of the analytical assays described herein. Similarly, liable chemical tags from sets of the capture particles can be liberated from their associated complexes while the complexes remain on their respective sorting membranes, the liable chemical tags disclosed in Huff et al (WO2016161402A1), which is hereby incorporated by way of reference.

In an example, elution (e.g., of (k) or (q)) is omitted, such that the sorted complexes remain on their sorting membranes, and the one or more analytical assays (e.g., of (l) or (r)) are subsequently carried out on the complexes remaining on the sorting membranes. As an additional example, each analyte of the sorted complexes are labeled with unique third binding agents, each unique third binding agent bearing an unique fluorophore or quantum dot that endows a distinct fluorescent emission spectrum to each labeled complex on the respective sorting membranes, and the fluorescent emission spectra of each labeled complex detected by a variety of optical modalities. Of course, other examples are possible and these examples are merely provided for exemplary purposes.

In an aspect, the present disclosure further provides a method for a direct assay to determine the presence or absence of at least one analyte of interest within a biological sample, by recording the optical diffraction spectra of microslit filters after the filtration step to observe any potentially isolated complexes as indicative of the at least one analyte's presence.

In an example, a method of a direct assay for determining the presence or absence of an analyte of interest in a biological sample (e.g., biofluid) comprises:

(s) adding one or more first binding agent to a biological sample (e.g., biofluid) such that at least two or more first ligands on at least one analyte are bound by the first binding agent, forming a complex of at least one analyte molecule bound by at least two or more first binding agent molecules;

(t) adding a plurality of capture particles (e.g., of diameter less than the width of the microslit filter openings) to the mixture of biofluid and binding agent, such that the first binding agents are bound by multiple capture particles, forming aggregates incorporating multiple complexes of first binding agents bound by capture particles and analytes bound by binding agents;

(u) contacting the biological sample (e.g., biofluid)-complex mixture with a microslit filter (with openings of width greater than the diameter of the capture particles), such that the aggregated complexes are retained by the microslit filter and undesired species and non-complexed components permeate through the microslit filter;

(v) recording the optical diffraction spectrum of the microslit filter of (o) (e.g., a sample optical diffraction spectrum); and (w) comparing the optical diffraction spectrum of (p) to an optical diffraction spectrum of a reference optical diffraction spectrum (e.g., the native microslit filter).

In an example, the capture particles' diameter, the microslit filters' openings, the first binding agent, and the binding capacity of the capture particles should be specified to promote the formation of complexes in aggregate form, wherein multiple analytes are bound by multiple first binding agents, and these multiple analyte-first binding agent complexes further bound by multiple capture particles. The capture particles' diameter should be less than the microslit filters' openings, so that in the absence of the analyte (i.e., no aggregates), non-complexed binding agent-capture particles should pass through the microslit filter. By contrast, in the presence of the analyte (i.e., where aggregates are formed), complexed analyte-binding agent-capture particles should be retained by the microslit filter.

In an example, first binding agents (e.g., of (s)) is specified such that at least two or more first binding agent molecules bind at least two or more distinct first ligands of one analyte molecule. More favorably, multiple first ligands of the analytes are bound by a first binding agent. In an example, the first binding agent comprises a polyclonal antibody, where the polyclonal antibody binds at least two or more distinct first ligands of the analyte. In another example, the first binding agent comprises two monoclonal antibodies, where each monoclonal antibody binds a distinct first ligand of the analyte. Of course, other possibilities could be used and these examples are merely provided for exemplary purposes.

The addition of the plurality of capture particles (e.g., of (t)) should be specified such that the added molecular binding capacity of the capture particles is less than the molecular number of analyte-first binding agent complexes. For purposes of this disclosure, the molecular binding capacity of the capture particles equals the number of molecular analyte-first binding agent complexes bound per capture particle. To promote the formation of aggregates with multiple capture particles and analyte-first binding agent complexes, it is desired that multiple capture particles bind one analyte-first binding agent complex, and as this is repeated, aggregates are formed. Accordingly, the ratio of molecular analyte-first binding agent complexes to complex binding capacity should be greater than 1:1. In various examples, the ratio is 2:1 to $10^7$:1, or any ratio value and range therebetween. As an example, if microslit filters with 9×50 μm openings are used in combination with 6-8 μm diameter capture particles, then aggregates incorporating at least 9 capture particles should be formed in order for the aggregates to be retained, and the ratio of analyte-first binding agent complexes to capture particles' binding capacity should be specified accordingly to promote aggregates of at least this size.

In an example, filtration (e.g., of (u)) is performed using any of the flow modalities previously described for the filtration (e.g., of (c)).

In an example, where the one or more first binding agents are directly coupled to one more sets of the plurality of capture particles (e.g., of (s) and (t)) of the method is performed simultaneously as one active step and the second binding agent (e.g., of (t)) is omitted.

In an example, an upstream sample preparation step (e.g., of (m) precedes the steps of the direct assay method (e.g., of (s) through (w)), such that contacting the biological sample (e.g., biofluid) with a microslit filter provides a sample where undesired species are retained by the microslit filter and desired species permeate through the microslit filter for subsequent analysis by the direct assay method.

In an example, detecting the presence of the analyte of interest is dependent on observable differences between the sample and reference optical diffraction spectra. In its native state (i.e., not used in filtration steps), the periodic openings of microslit filters can cause coherent light to be diffracted and a repeatedly observable diffraction pattern or spectrum generated. These consistent diffraction spectra are generated upon trans-illumination with a coherent light source (e.g., laser of specified wavelength) and thus are well-suited to serve as a reference for comparative purposes. However, the retention of aggregated complexes by the sample microslit filter disrupts its periodicity and thus distorts its optical diffraction upon trans-illumination with the same coherent light source. Therefore, observable differences between the sample and reference spectra is indicative of the presence of the aggregated complexes on the sample microslit filter.

In an example, a signal processing algorithm is used to record, collect, and compare the sample and reference optical diffraction spectra for purposes of detecting the presence of aggregated complexes. The extent of the differences between sample and reference optical diffraction spectra may be used to quantitate the concentration of the analyte of interest in a biofluid sample and may require the generation of a series of reference optical diffraction spectra. Optical diffraction spectra from each instance of the series are recorded, where aggregates are formed and retained by microslit filters and a known concentration of analyte used in each instance of the series. The sample optical diffraction spectrum would be compared to the reference series in order to determine the concentration of analyte within the biofluid sample. A linear regression or other appropriate statistical method may be employed for the comparison of the sample spectrum to the reference series spectra. As one example, the signal processing algorithm is used to compare the intensity or magnitude of first, second, third, and successive diffraction order peaks, where any differences in the intensity of any such diffraction order peaks between reference and sample diffraction spectra comprises a potential measure for quantitating the concentration of an analyte of interest that is captured in aggregated complexes. In this example, it is assumed that retained aggregated complexes that disrupt the periodicity of trans-illuminated microslit filters cause quantitative changes in diffraction order peak intensities (e.g., reduction in some peaks, appearance of new diffraction order peaks, or increases in other diffraction order peaks), and that these diffraction order peak changes may be observed when comparing reference and sample diffraction spectra.

In a further example, the signal processing algorithm permits the real-time detection of an analyte of interest. For example, quantitative changes in diffraction order peaks (when comparing reference and sample diffraction spectra) are used in real-time measurements as aggregated analyte-binding agent-capture complexes are formed and isolated by a microslit filter. In this example, any of the flow modalities disclosed herein are used to isolate any aggregated complexes as they are formed in real-time, and the direct assay method of the present disclosure used to quantitatively detect any such aggregated complex formation and isolation events.

In examples where the biofluid is whole blood, the width of the microslit filter openings are specified such that they retain or allow permeation of hemocytes (i.e., leukocytes, erythrocytes, and platelets) as the free, unbound and unwanted blood constituents, depending on desired filtration outcome. In examples where hemocyte permeation is desired, the width of the openings in the microslit filters are 7 to 9 µm, including every 0.1 µm value and range therebetween, as this width of opening allows hemocyte permeation. By contrast, in examples where hemocyte retention is desired, the width of the openings in the microslit filters are less than or equal to 2 µm, as this width of opening retains hemocytes.

In examples where the biofluid is urine, the width of the microslit filter openings are specified such that they retain or allow permeation of hemocytes (i.e., leukocytes, erythrocytes, and platelets), urothelial cells, and protein aggregates (e.g., Tamm-Horsfall protein filaments), as the free, unbound and unwanted constituents, depending on desired filtration outcome. In examples where cellular and/or protein aggregate permeation is desired, the width of the openings in the microslit filters are 7 to 9 µm, including every 0.1 µm value and range therebetween, as this width of opening allows permeation of these species. By contrast, in examples where cellular and/or protein aggregate retention is desired, then the width of the openings in the microslit filters are less than or equal to 2 µm, as this width of opening retains these species.

In further examples, the width of the microslit filter openings are specified such that they retain or allow permeation of capture particles, depending on desired filtration outcome. For example, if capture particle retention is desired, the capture particles used in combination are greater than 9 µm in diameter, whereas if capture particle permeation is desired, the capture particles used in combination are less than 9 µm in diameter. In an example, where concurrent removal of hemocytes and retention of aggregated complexes are desired, capture particles are less than 9 µm in diameter.

In an example, one or more analytes are found in a biofluid sample and comprise one or more species of diagnostic or prognostic utility, such as circulating cell-free DNA or RNA, circulating cell-free nucleosomes or dinucleosomes, circulating extracellular vesicles, circulating tumor cells, infectious pathogens, or protein biomarkers. Isolation and analysis of one of these analytes is often desired to diagnose a disease (e.g., cancer, auto-immune syndrome, and the like) or infection (e.g., uremia, bacteremia, and the like) and a method of this disclosure is used for purposes of isolating an analyte for diagnoses or prognoses. Further, a method of this disclosure is used for purposes of isolating an analyte for a liquid biopsy, where the biofluid sample is whole blood, plasma, or serum, or the like. In a further example, a method of this disclosure is used for purposes of isolating an analyte for a liquid biopsy, where the biofluid sample is urine.

In another example, multiple analytes of diagnostic and/or prognostic value are found in a biofluid sample and a method of this disclosure is used to isolate the multiple analytes for purposes of providing a more comprehensive range of samples for diagnoses, prognoses, or liquid biopsies. For example, the multiple analytes are samples usually isolated individually by other means for purposes of carrying out a disease diagnostic or for monitoring responses to treatment (e.g., cancer and its response to chemotherapeutics). As one possible example of a cancer liquid biopsy, analytes of interest include circulating tumor cells, circulating extracellular vesicles, and circulating cell-free nucleic acids (e.g., DNA in some nucleosomal form). First binding agents bind these three analytes in a blood sample, sets of the plurality of capture particles (of 10, 14, and 18 µm diameter) each distinctly capture one of the three analyte-first binding agent complexes, the complexes isolated by 9 µm opening microslit filters, retained complexes eluted off the microslit filters and the distinct sets of capture particles and their associated complexes further sorted into distinct populations using sorting membranes with openings of 10, 14, and 18 µm. Any of the analytical assays listed above is carried out on the three isolated fractions (e.g., sequencing reactions to identify possible genetic mutations associated with cancer).

In an example where nucleic acids are isolated for diagnostic purposes, the biofluid is mixed with capture particles comprising an anion exchange solid phase support (e.g. silica particles) that are well-known by those skilled in the art to bind nucleic acids under specified ionic and pH conditions (Tien et al, 2000). For example, the biofluid could be mixed with a lysis buffer, comprising a chaotrope (e.g., guanidium HCl and the like), a detergent (e.g., Triton X-100, sodium dodecyl sulfate, and the like), an alcohol (e.g., isopropanol and the like), a chelator (e.g., ethylene diamine tetra-acetic acid, EDTA, and the like), a buffer (e.g., 2-Amino-2-(hydroxymethyl)propane-1,3-diol, Tris HCl, pH≤6.5, and the like), and, optionally, a proteolytic enzyme (e.g., proteinase K and the like). Next, the lysate is mixed with silica particles of specified diameter (e.g., 10 μm), such that the nucleic acid content of the lysate is bound by the silica particles, and the particles contacted by a microslit filter of specified dimension (e.g., openings of 8 μm width). The captured silica particles could be washed to remove nonspecifically bound contaminants using a wash buffer (e.g., comprising isopropanol and Tris HCl pH≤6.5). Finally, the nucleic acids are eluted from the silica particles using water or Tris-EDTA buffer (pH≥8.5), or alternatively, the capture particles eluted under conditions wherein the nucleic acid remain bound to the silica particles, or one or more of the analytical assays described herein performed on the silica particles.

In examples of the various methods of this disclosure, where the biofluid sample is whole blood, and the blood sample is obtained from a donor by means of a venous puncture blood draw or an arterial blood draw. The receptacle or vessel into which the drawn blood is received provides in situ the means for anti-coagulating the blood (e.g., EDTA, heparin, and the like). The receptacle or vessel serves as the incubation volume into which the first binding agent and/or capture particles are added in order to form the analyte-first binding agent-capture particle complexes.

In some examples of the indirect assay methods, wherein the analyte of interest is a living organism (i.e., among those listed above: cells, bacteria, or fungi), an additional incubation period providing time for culture, growth and/or expansion of the isolated living species is incorporated. In these examples, the subsequent analytical assays may include phenotypic or functional tests, following or during the additional incubation period. In an example, the phenotypic or functional assays are combined with one or more of the previously listed assays. During the additional incubation period, appropriate environmental conditions and nutrient supplies are furnished to the living species, having eluted them from the isolating microslit filters and transferred them to vessels appropriate for their culture. The sterility of the collected biofluid sample, the device and reagent components, and the related methods is maintained for proper growth and culture. As an example of the additional incubation period and phenotypic/functional assay, an isolated circulating tumor cell could be clonally expanded and the growth of multiple derived clonal cultures challenged by a panel of chemotherapeutic agents to identify potential best therapies. As another example, an isolated bacterium is clonally expanded and the growth of multiple derived clonal cultures challenged by a panel of antibiotic agents to assess phenotypic antibiotic resistance.

In an aspect, the present disclosure provides fluidic devices for carrying out the methods of the disclosure. In various examples, these fluidic devices include one or more microslit filters for isolating analyte-affinity moiety-complexes and/or sample preparation, as well as one or more additional sorting membranes for resolving distinct sets of such complexes into separate fractions. In an example, the fluidic device comprises at least one microslit filter. In an another example, the fluidic device comprises at least one microslit filter and at least one sorting membrane In a further aspect, the thickness, porosity, and opening aspect ratio of microslit filters are specified in examples disclosed herein, such that the thickness and porosity properties promote low species permeation resistance and high permeability (i.e., high permeation capacity, low pressure operation), while the opening aspect ratio promotes non-fouling behavior and precision molecular cut-off (i.e., isolation and retention of desired complexes and removal of undesired species, complexes, and non-complexed species). In further examples, the characteristics of microslit filters are specified for performing an upstream sample preparation as disclosed herein.

In a further aspect, the characteristics of capture particles are specified by examples disclosed herein, such that the capture particles allow retention and isolation of formed analyte-affinity moiety-capture particle complexes and the permeation of undesired species and complexes, as well as removal of non-complexed components. In these examples, the diameter of the capture particles are specified with respect to width and aspect ratio of the openings of the microslit filters, or with respect to the openings of sorting membranes, that will be used in conjunction with the capture particles to affect the desired filtration outcome. Furthermore, one or more physical properties of the capture particles are specified in combination with its diameter to provide a means of identifying a distinct set of a plurality of capture particles.

In an example of the present disclosure, a device for capturing and isolating an analyte of interest from a biofluid comprises a fluidic device comprising one or more microslit filter elements, having at least one chamber or channel in fluidic contact with the cis-side of the microslit filter and at least one chamber or channel in fluidic contact with the trans-side of the microslit filter, where the cis and trans-sides oppose each other, and the cis- and trans-side chambers or channels are fluidically connected by a plurality of openings in the one or more microslit filters.

The microslit filters of the fluidic device have specified physical characteristics to promote high cis-to-trans permeation of biofluid-complex mixtures and to promote non-fouling behavior and precision molecular cut-off. The microslit filters comprise a plurality of arrayed openings that fluidically connect their opposing cis- and trans-sides. In an example, the microslit filters have a range of thickness; the thickness is from 50 nm to 25 μm, including all nm and μm values and ranges therebetween. The microslit filters can have a range of porosity; for example, the porosity can be from less than 1% to 75%, including all integer percent values and ranges therebetween. The microslit filter can have a range of aspect ratio for its openings; for example, its openings are cubic prisms, rectangular prisms, or trapezoids and are 0.5 μm to 15 μm in width and 5 μm to 100 μm in length, including all nm and μm values and ranges therebetween thus possessing a range of aspect ratio (in terms of width to length) between 1:0.33 to 1:200. In an example, the microslit filter is 400 nm thick, has approximately 17% porosity, and has openings of 9 μm width and 50 μm length, and an aspect ratio of 1:5.5. In another example, the microslit filter is 400 nm thick, has approximately 9% porosity, and has openings of 1 μm width and 50 μm length, and an aspect ratio of 1:50. Of course, other values are possible and these are merely listed as examples.

The microslit filters of the fluidic devices should be further specified so that contacting the biofluid and/or the mixture of biofluid and analyte-first binding agent-capture particle complexes performs the desired filtration steps of the present disclosure. Accordingly, the microslit filters of the fluidic device should be specified in terms of the width of their openings to retain biofluid species and/or a set of the complexes, to permeate other species and/or sets of complexes, and to permeate free, non-complexed species. The diameter of capture particles must be specified with respect to the width of the microslit filter's openings in order to affect the desired retention or permeation outcomes. Further, the relative size of biofluid species (e.g., cells and/or protein aggregates) is considered with respect to the width of the microslit filter's openings in order to affect the desired upstream sample preparation (e.g., species retention or permeation) outcomes.

The fluidic device can accomplish the filtration (e.g., of (c), (h), (m), and/or (u)) using several flow modalities and filtration system configurations. In an example, the fluidic device uses dead-end filtration, where contact with the microslit filter involves flow that is normal to the microslit filter surface. The biofluid or biofluid-complex mixture is introduced to the cis-side of the filter and either hydrostatic pressure or the application of cis-side positive pressure or trans-side negative pressure initiates flux from the cis- to the trans-side of the filter. Positive and negative pressures are generated by gravity/hydrostatic pressure or by pumping, vacuum, gas pressurization, or centripetal force. In various examples, the fluidic device is a stirred cell dead-end filtration system that uses gas pressurization or vacuum, or the fluidic device is a centrifuge insert dead-end filtration system that uses centripetal force. In another example, the fluidic device uses transmembrane pressure differential and tangential flow, where contact with the microslit filter involves flow that is tangential to the microslit filter surface, the biofluid or the biofluid-complex mixture is introduced to the cis-side of the filter, bulk flow is initiated on both cis- and trans-sides of the filter such that a transmembrane pressure is generated (i.e., relative negative pressure on the trans-filter side), thus initiating flux from the cis- to the trans-side of the filter. The relative bulk flow rate on the cis-filter side should be greater than the bulk flow rate on the trans-filter side in order to create the desired transmembrane pressure vector. In various examples, the cis- and trans-sides of the microslit filters are fluidically connected to chambers or channels of these opposing sides and bulk flow is initiated in these chambers or channels using gas pressurization or pumping apparatus (e.g., a syringe or peristaltic pump). In various examples, the fluidic device is a tangential flow filtration system.

The fluidic device of the present disclosure can further comprise one or more sorting membrane elements, comprising sorting membranes with opposing cis and trans-sides that are fluidically connected via a plurality of openings, and are further fluidically connected to two or more opposing cis and trans-side chambers or channels. The fluidic device can comprise independent or combined microslit filter and sorting membrane elements. As an example, the fluid is initially contacted by a microslit filter element, the fluid is then passed to and contacted by one sorting membrane element or by a first sorting membrane element, and then the fluid is passed to and contacted by a second sorting membrane element, wherein these one or more elements are independent and connected by tubing or channels with inlets and outlets between the one or more elements' respective fluidic chambers. In an alternative example, a microslit filter, a first sorting membrane, and a second sorting membrane are elements of one combined substrate and are disposed along the length of one channel, such that the fluid is successively contacted by each element as it passes through the channel, wherein the microslit filter and one or more sorting membrane elements are fabricated on distinct regions of one substrate. In these examples, the cis-side of the microslit filter is in fluidic connection with the cis-sides of the two sorting membranes (i.e., all of the same plane within the fluidic device). Of course, other combinations and configurations of these elements are possible and these examples are merely provided for exemplary purposes.

The fluidic devices could accomplish any washing steps (following the filtration or sorting steps) using similar flow modalities and filtration system configurations as those used for filtration or sorting steps. For example, in a stirred cell filtration system or a centrifuge tube insert filtration system (both of which are configured for dead-end/normal flow), one or more bolus of fresh buffer is introduced to the cis-side of the microslit filter (following the filtration step), and either hydrostatic pressure or the application of cis-side positive pressure or trans-side negative pressure initiates flux of the buffer. In an additional example, in a tangential flow filtration system (configured for tangential flow), one or more bolus of fresh buffer is introduced to the cis-side of the microslit filter and/or sorting membranes (following the filtration and sorting steps), and bulk flow on the cis-side used to initiate buffer flow. Application of transmembrane pressure is optional in this latter example.

The fluidic devices could accomplish the elution (e.g., of (d), (i) (k), or (q)) using similar flow modalities and filtration system configurations as those used for filtration and sorting steps. However, in some examples, the fluidic devices should be able to operate the flow modality in reverse of that initially used for the filtration and/or sorting steps. As one example, the retained complexes is eluted from the cis-side of a microslit filter by introduction of a bolus of buffer to the cis-side of the contacting microslit filter, resuspension of the complexes by any mechanical mixing method, and the resuspended complexes removed from the fluidic device (e.g., by a manual or automated pipet). As another example, the pressurization within a stirred cell filtration system is reversed, following an introduction of fresh buffer to the cis-side of the contacting microslit filter, and the pressurization used to flush off retained complexes into the buffer. As yet another example, the relative bulk flow rates and direction of the transmembrane pressure vector is reversed in a tangential flow system to flush off retained and/or sorted complexes into a flow of fresh buffer introduce to the cis-side of the contacting microslit filter.

The same flow modalities used by the fluidic devices for elution of complexes could be used for disrupting complexes and for recovery of their derived species. For example, these flow modalities are used for introduction of a buffer containing either a chemical reagent that breaks covalent bonds of the complex' species or a molecular excess of a competitively binding ligand to disassociate analytes from their binding agents. Alternatively, a buffer of specified pH or salt concentration is introduced to disrupt complexes. In these examples, the liberated species of the complexes is recovered in the volume of introduced buffer. Similar elements are used in fluidic device examples where liable tags of the capture particles are liberated by any of the means described herein.

In an example, the fluidic devices further comprise an element for the disruption of retained complexes. For example, the fluidic devices comprise a transducer for mechanical sonication of complexes, a heating element for heat denaturation of complexes, or a UV light source for the photolysis of complexes. Similar elements are used in fluidic device examples wherein labile tags of the capture particles are liberated by any of the means described herein.

In an example, sorting membranes of the fluidic devices are specified to promote accurate capture of one set of capture particles or resolution of distinct sets of capture particles and for carrying out the sorting of (j) and/or (p). Sorting membranes have a range of thickness; for example, the thickness is 50 nm to 25 μm, including all nm and μm values and ranges therebetween. Sorting membranes have a range of porosity; for example, the porosity is from less than 1% to 75%, including all integer percent values and ranges therebetween. Sorting membranes have a range of aspect ratio for its openings; for example, its openings are cylindrical pores and are 10 nm to 50 μm in diameter, including all nm and μm values and ranges therebetween. In an additional example, sorting membranes openings' are cubic prisms, rectangular prisms, or trapezoids and are 0.5 μm to 15 μm in width and 5 μm to 100 μm in length, including all nm and μm values and ranges therebetween, thus possessing a range of aspect ratio (in terms of width to length) between 1:0.33 to 1:200. In a particular example, the sorting membrane is 400 nm thick, has approximately 20% porosity, and has 0.5 μm diameter pores. In another particular example, the sorting membrane is 100 nm thick, has approximately 17% average porosity, and has 50 nm average diameter pores. Of course, other values are possible and these are merely listed as examples.

In an example, one or more sorting membranes of the fluidic device are configured in series and are of the same plane or of successive planes. In an example configuration, both cis-sides of two sorting membranes are in fluidic connection with the cis-side of a microslit filter, thus all three elements are of the same plane. In an alternative example configuration, the cis-side of a first sorting membrane is in fluidic connection with and of the same plane as the cis-side of a microslit filter, and the cis-side of a second sorting membrane is in fluidic connection with the trans-side of the first sorting membrane (the first and second sorting membranes being of successive planes). In this alternative configuration, the first sorting membrane should permit the permeation of smaller diameter complexes through its openings, so that any second and subsequent sorting membranes are accessible to the smaller diameter complexes that permeate through the first sorting membrane. It is recognized that the first sorting membrane will sort the set of complexes with largest diameter, while each successive sorting membrane will successively sort complexes of decreasing diameter (if diameter is specified as the parameter used for sorting sets of complexes). In an alternative example configuration, the cis-side of one sorting membrane are in fluidic connection with the trans-side of a microslit filter, thus the sorting membrane and the microslit filter are of successive planes.

The further examples of the fluidic device, comprising microslit filter and sorting membrane elements, use tangential flow alone or tangential flow in combination with normal flow. As an example, tangential flow alone is used to contact the biofluid and/or the biofluid-complex mixture by the cis-sides of successively configured microslit filters and sorting membranes in either the independent or combined configurations if these elements are all of the same plane. As a different example, tangential flow is used to contact the biofluid-complex mixture by the cis-sides of a successively configured microslit filter and one sorting membrane or a first sorting membrane (these two elements being of the same plane), and then normal flow used to pass the resultant permeate of the first sorting membrane to the cis-side of a second sorting membrane (the first and second sorting membranes being of different planes). The fluid is successively transferred between elements either as continuous flow (passing fluid through all elements in uninterrupted succession) or as discrete flow (passing fluid one element at a time with interrupted flow at each element). Tangential and normal flow within these exemplary fluidic devices is initiated by the same bulk flow modalities described above. Accordingly, the further examples of the fluidic device is a tangential flow filtration system or a combined tangential/normal flow filtration system.

The microslit filters and sorting membranes of the fluidic devices comprise porous materials that can be fabricated by various methods. For example, these filters and membranes comprise a suspended membrane layer that was fabricated by: 1) patterning and etching the openings into silicon nitride or other Si-based film, using well-known photolithography and reactive ion etching methods, followed by etching to suspend the silicon nitride or other Si-based film by etching through a substrate (e.g., a silicon wafer); 2) embossing openings into polyurethane or poly-dimethyl-siloxane, using a master mould with a negative relief pattern of the openings; 3) solvent-casted polymer membranes of appropriate thickness and opening size and aspect ratio; 4) track-etched polymer membranes of appropriate thickness and opening size and aspect ratio; 5) patterned photoresist membranes (e.g., SU-8) with openings of appropriate size and aspect ratio that are fabricated by well-known photolithography methods (e.g., patterning SU-8 photoresist on a Si wafer and subsequent lift-off of the SU-8 membrane after its patterning); or 6) stainless steel, nickel or other alloy membrane with electro-formed openings of appropriate size and aspect ratio. In a further example, the sorting membrane is a nanoporous silicon nitride membrane (NPN). Examples of NPN membranes and the fabrication of such membranes are disclosed in U.S. Pat. No. 9,789,239 (Striemer et al. "Nanoporous Silicon Nitride Membranes, and Methods for Making and Using Such Membranes"), the disclosure of which with regard to NPN membranes is incorporated herein by reference. Of course, other microslit filter and sorting membrane materials and fabrication methods are possible and these examples are merely listed for exemplary purposes.

The microslit filters and sorting membranes of the fluidic devices have a specified thickness so that the fluidic device operates at a range of low pressurization when performing the filtration and sorting steps; e.g., 10 Pa to 1.0 kPa, and all Pa values and ranges therebetween.

Microslit filters and sorting membranes are incorporated into fluidic devices as independent or combined elements for carrying out the methods of the disclosure. For example, a microslit filter element comprising a suspended silicon nitride membrane is fabricated using a Si wafer and the resultant microslit filter incorporated into a fluidic device. As a further example, the previous microslit filter element can be incorporated into a fluidic device with one or more sorting membranes comprising suspended silicon nitride membranes, similarly fabricated on Si wafers. As another example, distinct regions of one Si wafer fabricated to correspond to a microslit filter and one or more sorting membrane, and this combination element incorporated into one fluidic device.

The microslit filters and sorting membranes can be functionalized with moieties that decrease the adhesion to biofluid constituents (e.g., coatings to reduce or prevent fouling). For example, a silanization process is used for functionalizing microslit filters and sorting membranes, where a vapor phase silane source contacts the filters or membranes, the silane reacts with a functional surface group of the filters or membranes, and the silane is further derivitized with a poly-ethylene glycol moiety of 5-10 carbon atoms in length, including all carbon length values and ranges therebetween. as another example, the microslit filters and sorting membranes could be functionalized with a carbenylation process (as disclosed in Shestopalov et al ((U.S. Ser. No. 15/130,208), which is hereby incorporated in its entirety by way of reference), wherein a vapor phase carbene source (e.g., a diazirine compound) contacts the filters and membranes, the carbene reacts with a functional surface group of the filters or membranes (e.g., an aliphatic monolayer), and the carbene is further derivitized with a poly-ethylene glycol moiety of 5-10 carbon atoms in length, including all carbon length values and ranges therebetween. In either example, the poly-ethylene glycol moieties serve as the coatings that reduce or prevent biofluid fouling. Furthermore, the addition of such coatings may ease elution of complexes off of the microslit filters and sorting membranes. Of course, these two examples are only two possibilities and are merely provided for exemplary purposes.

Alternatively, the silanization and/or carbenylation processes described herein could be used for functionalizing the surfaces of microslit filters and/or sorting membranes to promote their selective interactions with retained analyte-first binding agent-capture particle complexes. For example, a silanized or carbenylated surface is further derivitized with an affinity moiety or charged moiety, either of which may promote surface-complex interactions. For instance, a charged moiety with specified ionic properties could be used to promote surface-complex interactions at a specified pH). Of course, other means for promoting interactions between retained complexes and microslit filters and/or sorting membranes are possible and these examples have been provided for exemplary purposes.

The fluidic device may further comprise a light source and a detector for recording optical signals of any assay. The light source may be a laser, an LED, or any similar light source. The detector may be a spectrophotometer, a photometer, a leumeter, or any other similar device. The light source and detector may be appropriate for carrying out any of the analytical assays described herein, as performed on intact complexes that remain on microslit filters and/or sorting membranes. For example, the light source and the detector are configured as required by the optical assay method and used to read optical signals generated at the microslit filter and/or sorting membrane surfaces; for instance, the microslit filter or sorting membrane is disposed between the light source and the detector.

In an example, a fluidic device for direct assays for determining the presence or absence of an analyte of interest in a biofluid comprises at least one sample microslit filter, at least one reference microslit filter, a light source, and a detector, and is used to carry out the methods of the direct assay. In some examples, the sample and reference microslit filters are disposed between the light source and the detector, such that the microslit filters can be trans-illuminated by the light sources and their resultant diffraction spectra recorded by the detector. In a further example, a fluidic device for direct assays may further comprise an additional microslit filter, such that the additional microslit filter performs sample preparation prior to (i.e., upstream of) the direct assay methods. In some examples, the sample and reference microslit filters are disposed between the light source and the detector, such that the microslit filters are trans-illuminated by the light sources and their resultant diffraction spectra recorded by the detector. Any of the flow modalities and filtration system configurations described herein can be used for the filtration (e.g., of (u)). The fluidic device for the direct assay may further comprise a light source that trans-illuminates the microslit filter (e.g., sample and reference microslit filters) using coherent light (e.g., a laser of specified wavelength). The fluidic device of the direct assay may further comprise a signal processing algorithm, wherein the signal processing algorithm automates the collection and comparison of sample and reference microslit filter diffraction spectra. In some examples, multiple fluidic devices of the direct assay is configured such that multiple analytes (from one biofluid specimen) are analyzed on multiple sample microslit filters in parallel.

In an aspect, the present disclosure provides a kit comprising specified devices and reagents for carrying out the methods of the disclosure. Since the physical properties of microslit filters (e.g., thickness, porosity and opening aspect ratio and size) should be specified relative to capture particle size, and since microslit filter physical properties should be further specified for efficient processing of highly abundant species of biological samples, the devices and reagents of the disclosed kit are intended to be used as a combined system. Accordingly, in an aspect, a kit of the present disclosure comprises: a fluidic device, a plurality of capture particles, affinity moieties that bind one or more analytes, and affinity moieties that bind the analyte-binding affinity moieties.

In an example, a kit for capturing and isolating an analyte of interest from a biological sample (e.g., biofluid) comprises a fluidic device, one or more first binding agents, and a plurality of capture particles. The fluidic device of the kit comprises one or more microslit filter elements or one or more microslit filter and sorting membrane elements. The one or more first binding agents of the kit comprise one or more affinity moieties that bind one or more first ligands of the analytes of interest. The plurality of capture particles of the kit comprise one or more sets of capture particles that bind to the one or more first binding agents of the kit. The width of the microslit filters' openings and the capture particle's diameter of the kit are both specified such that analyte-first binding agent complexes are retained by the specified openings of the kit's microslit filters (i.e., the capture particles' diameter is greater than the width of the microslit filters' openings). The kit comprises elements to perform the methods of the disclosure disclosed herein.

In a further example, a further kit comprises one or more third binding agent, a light source, and a detector. The one or more third binding agents comprise affinity moieties that bind second ligands of the analytes that may be present in complexes on microslit or sorting membrane elements. The light source and the detector of the kit comprise elements for carrying out analytical assays on any labeled complexes that are present on microslit filter and/or sorting membrane elements.

In a further example, a further kit comprises one or more additional microslit filters for performing sample preparation.

In an example, a kit for the direct assay for determining the presence or absence of an analyte of interest in a biofluid comprises one or more fluidic devices for direct assays, one or more first binding agents, a plurality of capture particles, and can carry out the methods of the direct assay. In some examples, the kit further comprises a signal processing algorithm. In some examples, the kit further comprises additional microslit filters for carrying upstream sample preparation prior to the direct assay.

The fluidic device of the direct assay kit comprises at least one sample microslit filter, at least one reference microslit filter, a light source, and a detector. The one or more first binding agents of the direct assay kit comprise one or more affinity moieties that bind two or more first ligands of the analytes of interest. The plurality of capture particles of the kit comprise one or more sets of capture particles that bind to the one or more first binding agents of the kit. The width of the microslit filters' openings and the capture particle's diameter of the direct assay kit are both specified such that aggregated analyte-first binding agent complexes are retained by the openings of the kit's microslit filters, while non-complexed capture particles permeate through the microslit filters (i.e., the width of the microslit filters' openings is greater than the capture particles' diameter). In addition, a microslit filter is specified to retain or permeate species as desired for carrying out an upstream sample preparation. The light source, detector, and signal processing algorithm of the direct assay kit comprise elements for trans-illumination of sample and reference microslit filters and for recording, collecting, and comparing their respective diffraction spectra.

In the various examples of the kits disclosed herein, the one or more first binding agents can be directly coupled to the one or more sets of the plurality of capture particles.

In the various examples of the kits disclosed herein, the kits can further comprise buffers, chemical reagents, liable chemical tags, among other possibilities, for carrying out the washing, elution, complex disruption, and any other example of the methods disclosed herein.

The steps of the method described in the various embodiments and examples disclosed herein are sufficient to carry out the methods of the present disclosure. Thus, in an embodiment, a method consists essentially of a combination of the steps of one or more of the methods disclosed herein. In another embodiment, a method consists of such steps.

In the following Statements, various examples of the compounds, compositions, and methods of using the compounds and compositions of the present disclosure are described:

Statement 1. A device (e.g., a fluidic device) comprising: a microslit filter defining a plurality of openings.

Statement 2. The device according to Statement 1, further comprising a first fluidic channel or chamber on a side of the microslit filter and a second fluidic channel or chamber on an opposite side of the microslit filter.

Statement 3. The device of according to Statement 1 or 2, wherein the microslit filter has a thickness from 50 nm to 25 μm.

Statement 4. The device according to any one of the preceding Statements, where the microslit filter has a porosity from 1% to 75%.

Statement 5. The device according to any one of the preceding Statements, where the openings are cubic prisms or trapezoids.

Statement 6. The device according to any one of the preceding Statements, where the openings are rectangular prisms.

Statement 7. The device according to any one of the preceding Statements, where the openings have a width from 0.5 μm to 15 μm and a length from 5 μm to 100 μm.

Statement 8. The device according to any one of the preceding Statements, where the openings have an aspect ratio from 1:0.33 to 1:200.

Statement 9. The device according to any one of the preceding Statements, where the microslit filter is 400 nm thick and has 17% porosity, wherein the openings are 9 μm in width and 50 μm in length, and wherein the openings have an aspect ratio of 1:5.5.

Statement 10. The device according to any one of Statements 1-8, where the microslit filter is 400 nm thick and has 17% porosity, wherein the openings are 8 μm in width and 50 μm in length, and wherein the openings have an aspect ratio of 1:6.25.

Statement 11. The device according to any one of Statements 1-8, where the microslit filter is 400 nm thick and has 9% porosity, wherein the openings are 1 μm in width and 50 μm in length, and wherein the openings have an aspect ratio of 1:50.

Statement 12. The device according to any one of Statements 1-8, wherein the microslit filter is 400 nm thick and has 9% porosity, wherein the openings are 0.5 μm in width and 50 μm in length, and wherein the openings have an aspect ratio of 1:100.

Statement 13. The device according to any one of the preceding Statements, further comprising one sorting membrane element.

Statement 14. The device according to any one of the preceding Statements, further comprising at least two sorting membrane elements.

Statement 15. The device according to any one of the preceding Statements, where the sorting membrane further comprises nanoporous silicon nitride (NPN).

Statement 16. The device according to any one of the preceding Statements, further comprising a transducer for mechanical sonication, a heating element, and/or UV light source.

Statement 17. The device according to any one of the preceding Statements, where the microslit filter and/or sorting membranes are functionalized to decrease adhesion of biofluid constituents.

Statement 18. The device according to any one of the preceding Statements, where the microslit filter and/or sorting membranes are functionalized to increase interactions between retained complexes and the microslit filter and/or sorting membranes.

Statement 19. The device according to any one of the preceding Statements, further comprising a light source and a detector configured to record optical signals of an assay.

Statement 20. A method comprising:
  forming analyte-affinity moiety-capture particle complexes;
  filtering a sample thereby isolating desired analyte-affinity moiety-capture particle complexes and removing undesired analyte-affinity moiety-capture particle complexes, where the filtering uses the microslit filter according to any one of Statements 1-19; and
  optionally, eluting the retained intact analyte-affinity moiety-capture particle complexes and/or disassociating the retained analyte-affinity moiety-capture particle complexes to liberate their species.

Statement 21. The method according to Statement 20, further comprising performing at least one analytical assay on the retained analyte-affinity moiety-capture particle complexes and/or their liberated species.

Statement 22. The method according to Statement 20 or 21, wherein the analyte is one of intact cells, sub cellular components, proteins, nucleic acids, carbohydrates, lipids, peptides, viruses, bacteria, fungi, drugs, metabolites, low molecular mass species, or combinations thereof.

Statement 23. A method comprising:
- binding a first ligand on an analyte in a biofluid using a first binding agent thereby forming an analyte-first binding agent complex;
- adding capture particles to the biofluid, wherein the first binding agent is bound by the capture particles thereby forming an analyte-first binding agent-capture particle complex;
- filtering the biofluid having the analyte-first binding agent-capture particle complex with the microslit filter of the present disclosure (e.g., a microslit filter according to any one of Statements 1-19); and
- optionally, eluting or disassociating any of the analyte-first binding agent-capture particle complex that is retained from the microslit filter.

Statement 24. The method according to Statement 23, further comprising performing at least one analytical assay on a species of the analyte-first binding agent-capture particle complex.

Statement 25. The method according to Statement 23 or 24, where the analyte is one of intact cells, sub cellular components, proteins, nucleic acids, carbohydrates, lipids, peptides, viruses, bacteria, fungi, drugs, metabolites, low molecular mass species, or combinations thereof.

Statement 26. The method according to any one of Statements 20-25, where the biofluid is one of cell lysates, venous whole blood, arterial whole blood, plasma, serum, sputum, urine, cerebrospinal fluid, or conditioned cell culture media.

Statement 27. The method according to any one of Statements 20-26, where the first binding agent is one of monoclonal antibodies, polyclonal antibodies, fragments of monoclonal antibodies, fragments of polyclonal antibodies, DNA aptamers, RNA aptamers, peptides, modified peptide derivatives, lectins, bacteriophages, small molecules, or proteins, or combinations thereof.

Statement 28. The method according to any one of Statements 20-27, where the first binding agent is monovalent or multivalent.

Statement 29. The method according to any one of Statements 20-28, further comprising adding a second binding agent to the biofluid, where the second binding agent captures the first binding agent.

Statement 30. The method according to any one of Statements 20-29, where the capture agent is an organic material, an inorganic material, or a combined organic-inorganic material.

Statement 31. The method according to any one of Statements 20-30, where the filtering includes one of gravity flow, hydrostatic pressure, pumping, vacuum, centrifugation, gas pressurization, or tangential flow.

Statement 32. The method according to any one of Statements 20-31, where the filtering occurs at a pressure from 10 Pa to 1.0 kPa, including all Pa values and ranges therebetween.

Statement 33. The method according to any one of Statements 20-32, where the first binding agent includes two different types of the first binding agent, and where the capture particles include two different types of the capture particles.

Statement 34. The method according to any one of Statements 20-33, where the capture particles have a diameter less than a width of the microslit filter.

Statement 35. The method according to any one of Statements 20-34, where the capture particles have a diameter greater than a width of the microslit filter.

Statement 36. The method according to any one of Statements 20-35, where the method further comprises an upstream sample preparation.

Statement 37. A kit comprising one or more device of the present disclosure (e.g., one or more device according to any one of Statements 1-19) and one or more reagents (e.g., one or more reagents of the present disclosure) for carrying out a method of the present disclosure (e.g., a method according to any one of Statements 20-36).

Statement 38. The kit according to Statement 37, where the kit further comprises instructions for use of the one or more device (e.g., the one or more device according to any one of Statements 1-19) and/or one or more reagents (e.g., one or more reagents of the present disclosure).

Statement 39. The kit according to Statement 37 or 38, where the kit further comprises instructions for carrying out the method of the present disclosure (e.g., the method according to any one of Statements 20-36).

Statement 40. The kit according to any one of Statements 37-39, where the one or more reagents are selected from binding agents, capture particles, and combinations thereof.

Statement 41. The kit according to any one of Statements 37-40, where at least one of the binding agents are coupled to at least of capture particles.

Statement 42. The kit according to any one of Statements 37-41, where the binding agents are selected from affinity agents and combinations thereof.

Statement 43. The kit according to any one of Statements 37-42, where the kit further comprises one or more buffer, one or more chemical reagents, one or more liable chemical tags, for carrying out at least one of washing, elution or complex disruption.

Statement 44. The kit according to any one of Statements 37-43, where the kit further comprises a light source and/or a detector.

Statement 45. The kit according to any one of Statements 37-44, wherein the kit further comprises a signal processing algorithm.

The following examples are presented to illustrate the present disclosure. They are not intended to be limiting in any matter.

EXAMPLE 1

This example provides a description of examples of devices and methods of the present disclosure.

FIG. 1A shows a representative fluidic device incorporating a microslit filter, wherein the microslit filter is integrated into a centrifuge tube insert fluidic device for dead-end (normal) flow filtration purposes. FIG. 1B shows a representative microslit filter comprising 400 nm thick silicon nitride membranes, with three 0.7×3 mm suspended membranes, disposed on a silicon substrate of 5.4×5.4 mm and 0.3 mm thickness. The three 0.7×3 mm silicon nitride membranes further comprise a plurality of 8×50 μm openings patterned and etched through the 400 nm thick silicon nitride membranes. Conventional photolithography, reactive ion etching, and wet chemistry through-wafer etching were used to fabricate such microslit filters.

FIG. 2A shows the microslit filter of FIG. 1B before contact with a 0.5 mL solution containing approximately $10^6$ polystyrene beads of 10 μm diameter. FIG. 2B shows the microslit filter of FIG. 1B after contact with a 0.5 mL solution containing approximately $10^6$ polystyrene beads of 10 μm diameter. The microslit filter was first incorporated into the fluidic device of FIG. 1A and the solution containing the 10 μm diameter polystyrene beads was centrifuged at 300×G for 15 minutes to perform the filtration step. After the filtration step, the microslit filter was removed from the fluidic device and imaged by light microscopy.

Figure 2:
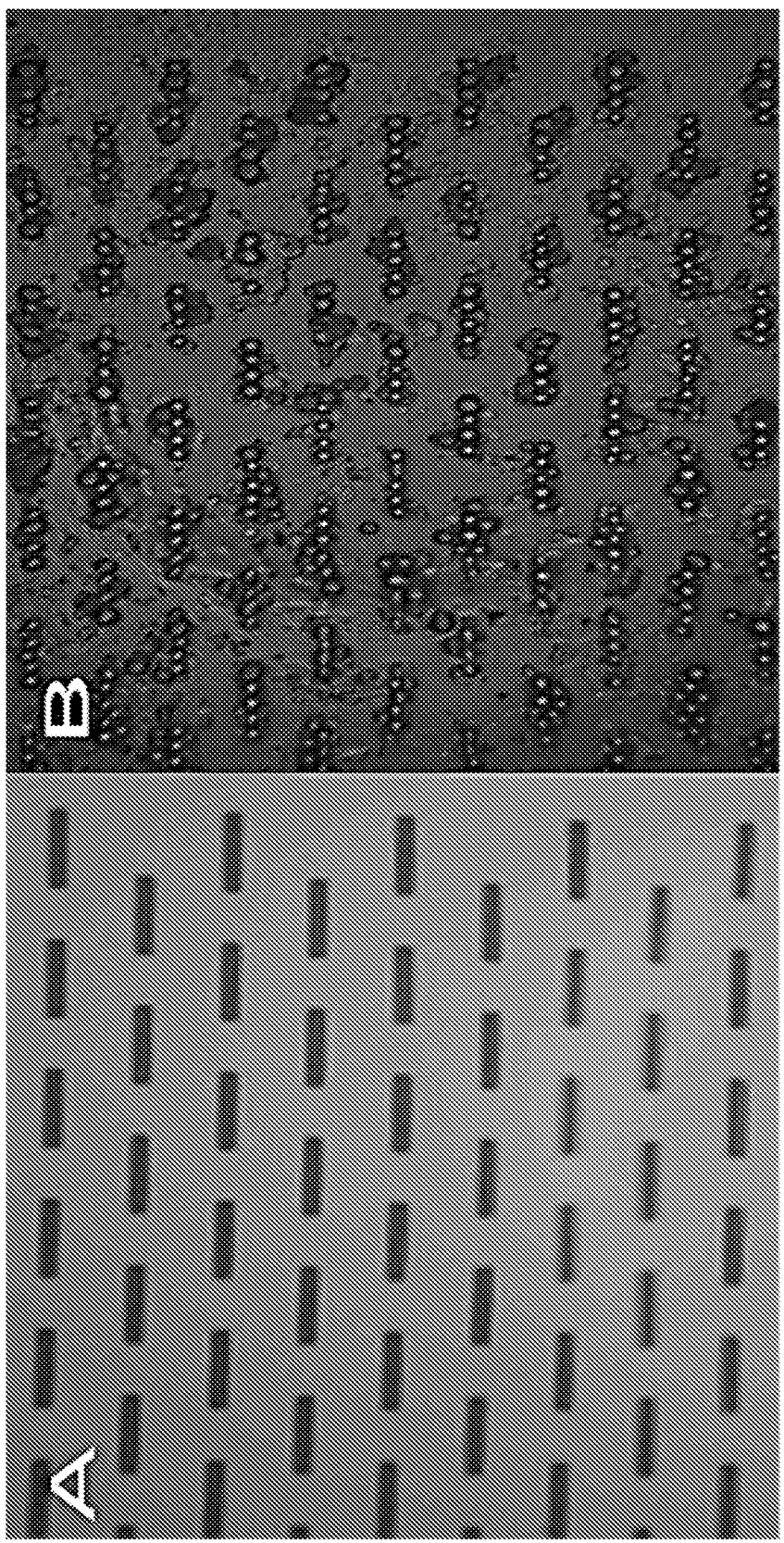
FIG. 2 shows (A) the microslit filter of FIG. 1B before contact with a 0.5 mL solution containing approximately $10^6$ polystyrene beads of 10 μm diameter (i.e., a clean membrane). (B) shows the microslit filter of FIG. 1B after contact with a 0.5 mL solution containing approximately $10^6$ polystyrene beads of 10 μm diameter.
Figure 3:
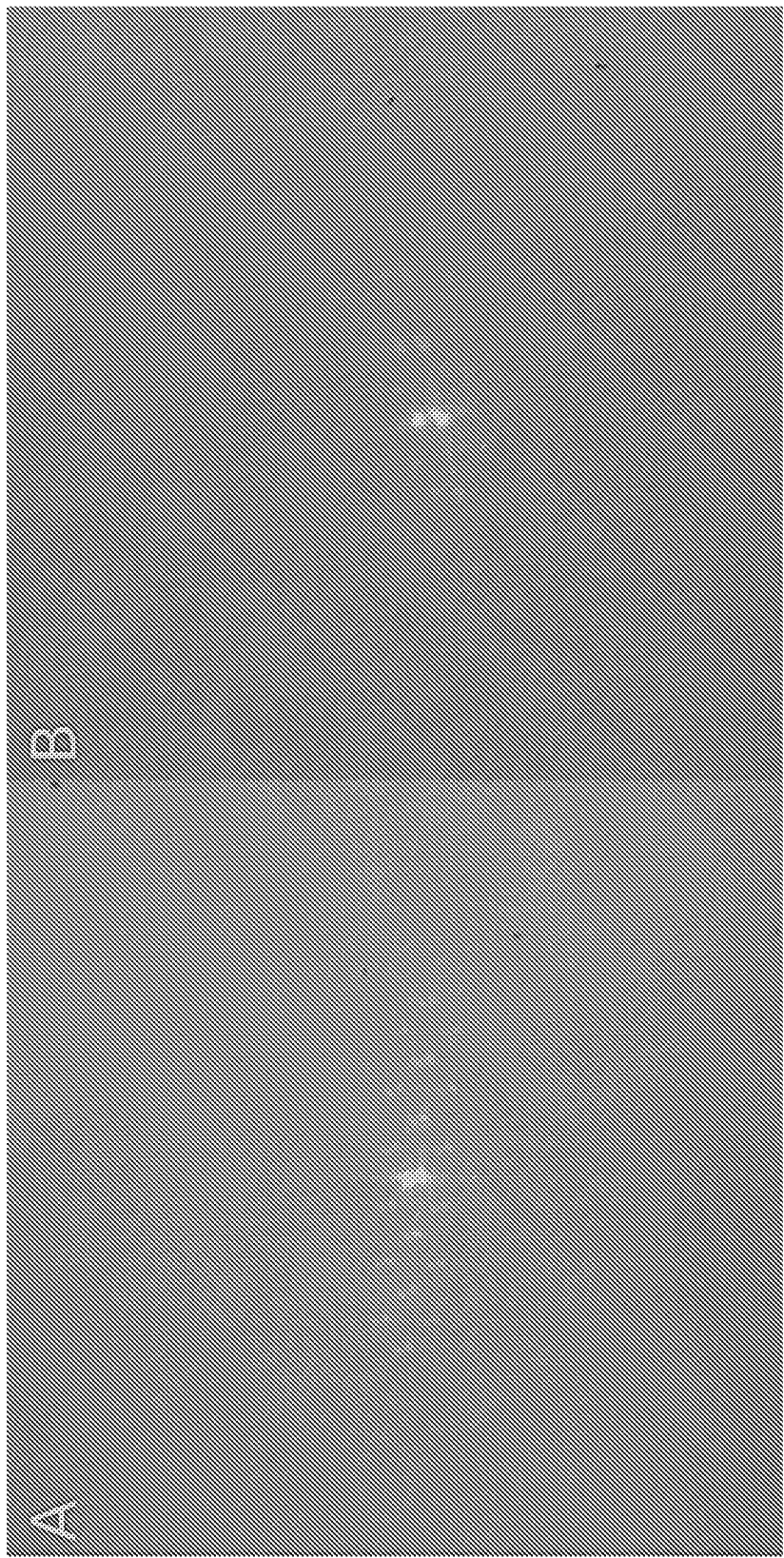
FIG. 3 shows (A) the native optical diffraction spectrum of the microslit filter of FIG. 1B (i.e., a reference diffraction spectrum) and (B) the resultant optical diffraction spectrum following the filtration example of FIG. 2 (i.e., a sample diffraction spectrum) (i.e., shows a sample pattern with beads blocking pores).

FIG. 3A shows the native optical diffraction spectrum of the microslit filter of FIG. 1B (i.e., a reference diffraction spectrum) and the resultant optical diffraction spectrum following the filtration example of FIG. 2 (i.e., a sample diffraction spectrum).

EXAMPLE 2

This example provides a description of examples of a method of the present disclosure.

Figure 4:
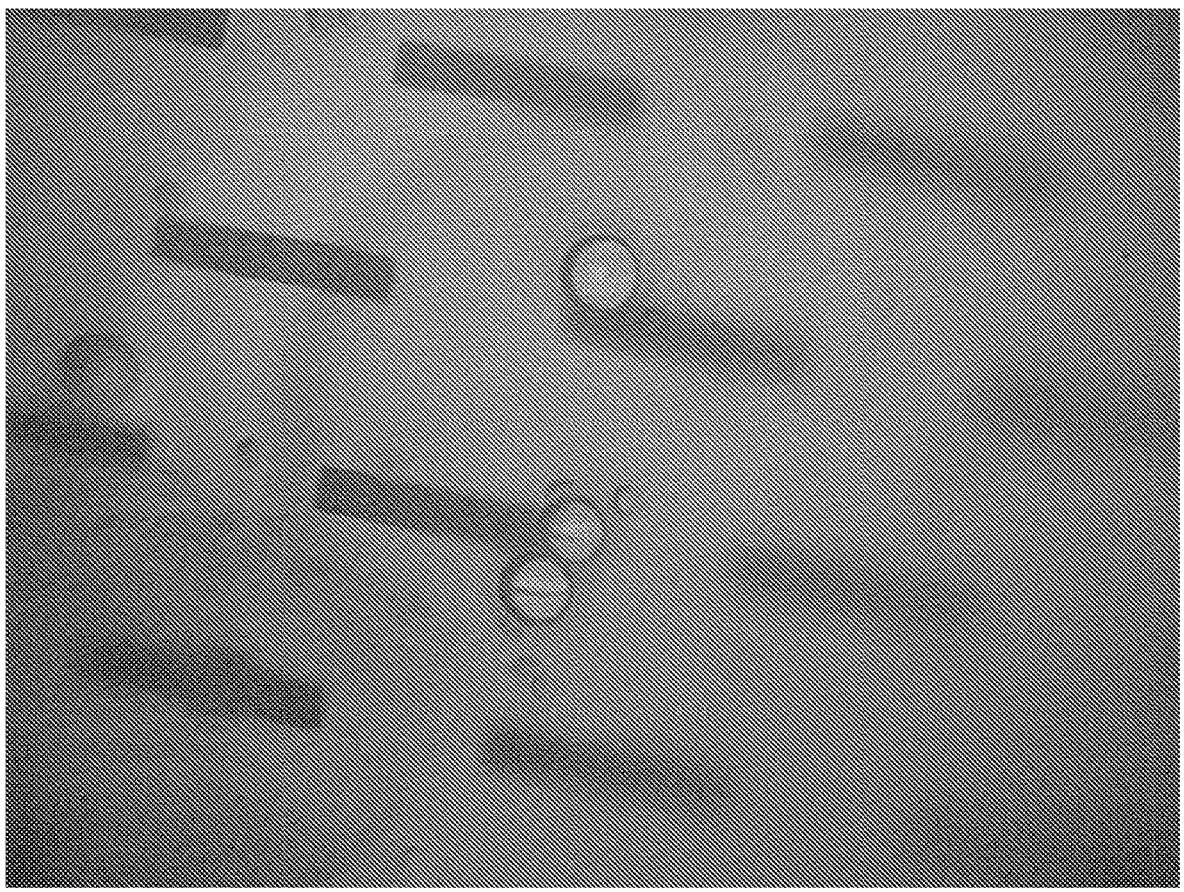
FIG. 4 shows anti-CD71 coated beads with cells bound on the membrane.

FIG. 4 shows the capture and isolation of a representative analyte from a biofluid sample. In this example, a 0.5 mL solution was incubated for 20 minutes at room temperature, comprising 250 μL human whole blood, 200 μL saline buffer, sodium heparin (2.5% final concentration), and 50 μL or ~106 beads of 10-13 μm diameter polystyrene beads coated with S. aureus Protein G that was bound to rabbit polyclonal anti-human CD71 antibody. CD71 is known as a cell surface marker for reticulocytes (Loken et al, 1987), an immature form of red blood cells, thus anti-CD71 antibody can be used to select reticulocytes from whole blood. Following the incubation, the solution was applied to the fluidic device of FIG. 1A and allowed to stand for 1 minute to accomplish hydrostatic pressure-driven filtration. The microslit filter was washed three times using 0.5 mL volumes of saline buffer, after which the microslit filter was removed from the fluidic device and imaged by light microscopy. The cells in close proximity to the beads are morphologically consistent with those of reticulocytes.

Figure 5:
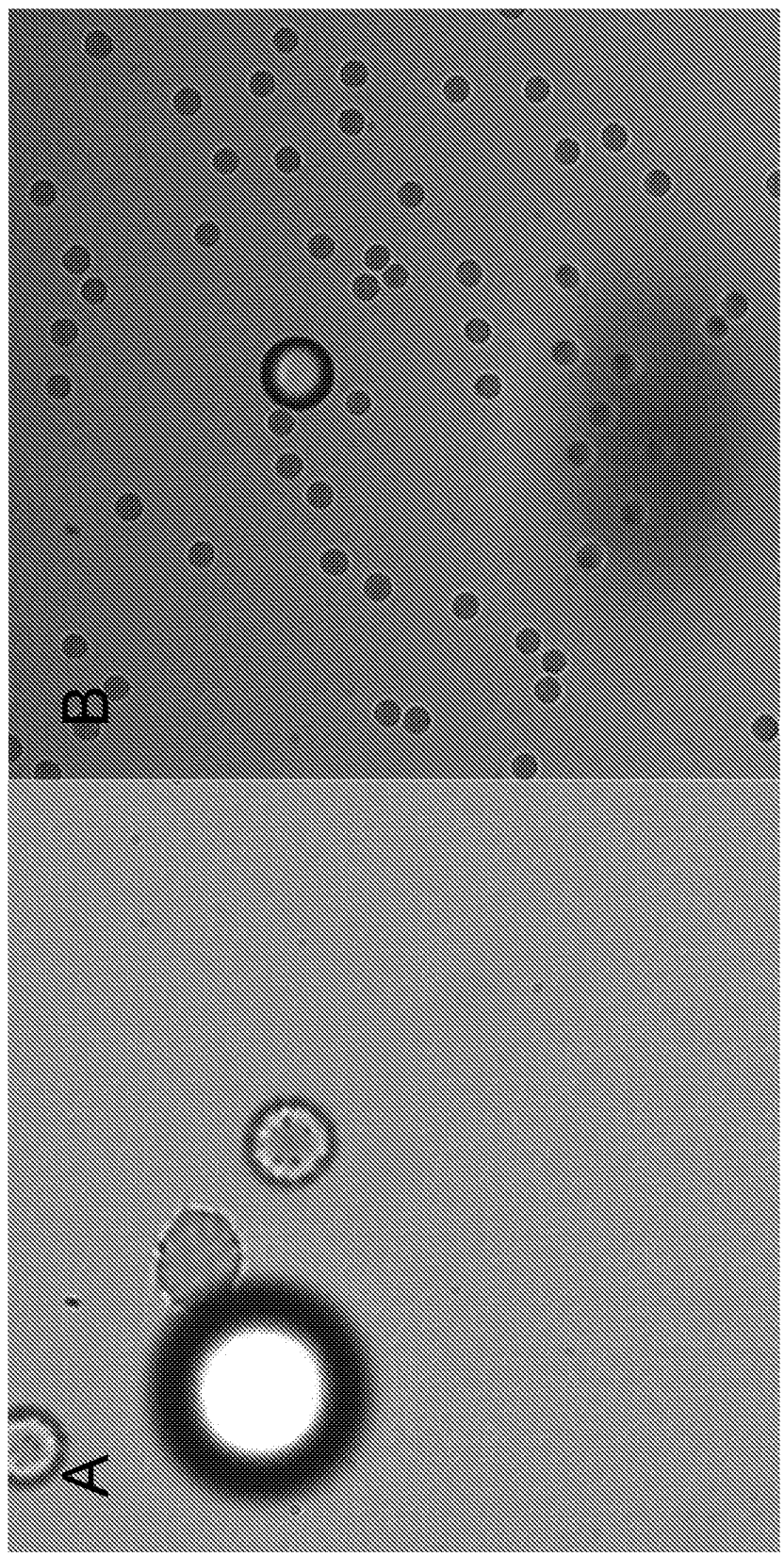
FIG. 5 shows (A) an anti-CD71 bead with a reticulocyte bound to the surface and (B) blocked/uncoated bead with no cells bound to the surface.

FIG. 5 shows the CD71+ cells recovered from the example of FIG. 4. The CD71+ cells were resuspended in 0.5 mL of saline buffer and transferred to a whole mount cell imaging chamber. FIG. 5A shows the CD71+ cells and capture beads at 60-times magnification and FIG. 5B shows the CD71+ cells and capture beads at 20-times magnification.

EXAMPLE 3

This example provides a description of examples of methods of the present disclosure.

Figure 6:
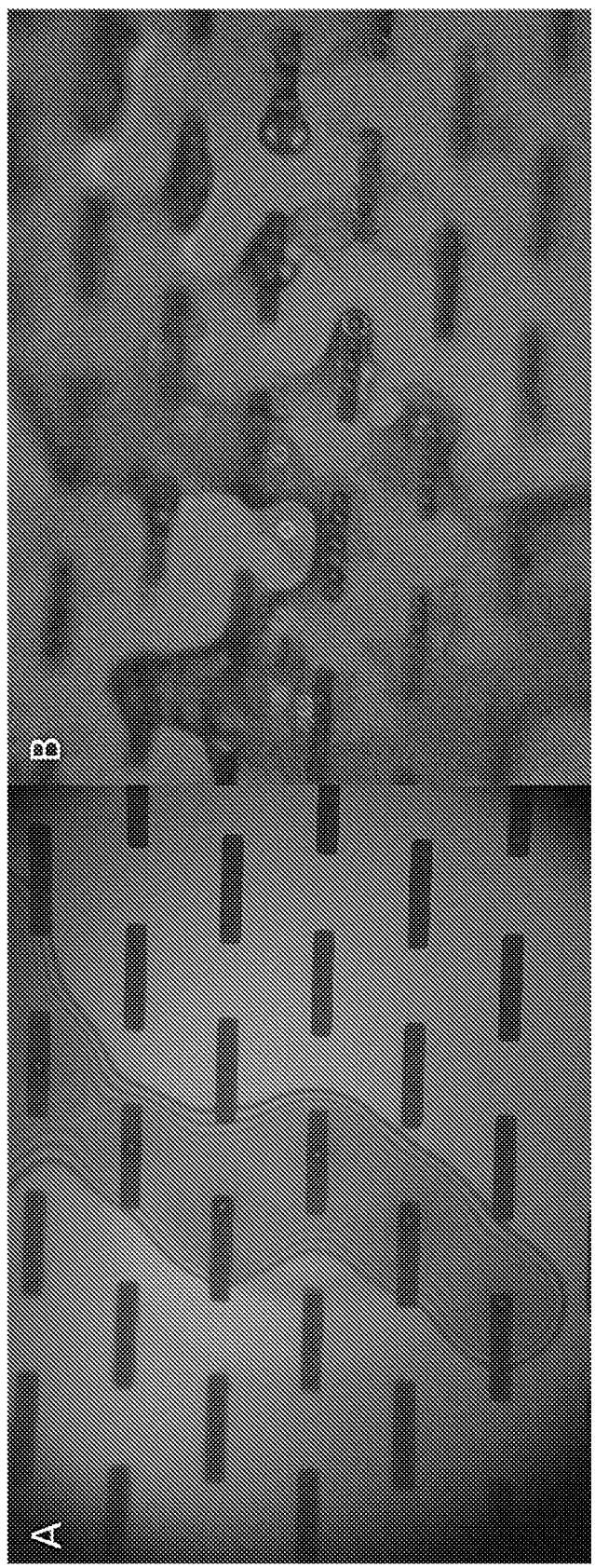
FIG. 6 shows a representative aggregation experiment. (A) shows the microslit filter before (top row) (only abnormally large beads were left behind) and (B) after (bottom row) filtration of the BSA (left column) or IgG (40 μL human IgG) (right column) solutions

FIG. 6 shows a representative aggregation experiment. A 1 mL solution was incubated for 20 minutes at room temperature, comprising either 40 μg of human immunoglobulin G (IgG) or 40 μg of bovine serum albumin (BSA), 6.8×10$^4$ polystyrene beads of 6-8 μm diameter coated with goat polyclonal anti-human IgG antibody, in a volume of saline buffer totaling 1 mL. Following the incubation, the solutions were centrifuged at 300×G for 5 minutes using fluidic devices incorporating microslit filters with 9×50 μm openings, three 0.7×3 mm membranes of 400 nm thick silicon nitride on 5.4×5.4 mm, and 0.3 mm thick silicon substrates. The microslit filters were removed from the fluidic devices following centrifugation for imaging by light microscopy. FIG. 6 shows the microslit filter before (A, top row) and after (B, bottom row) filtration of the BSA (left column) or IgG (right column) solutions. These incubations comprised approximately 1.5×10$^{14}$ IgG molecules and 6.8×10$^4$ beads, wherein the beads had a molecular binding capacity of 500,000 IgG molecules/bead. Thus the IgG-to-molecular binding capacity ratio was approximately, 4,383:1, and further, this example represents detection of an analyte at a concentration of 242 pM (based on IgG concentration).

Figure 7:
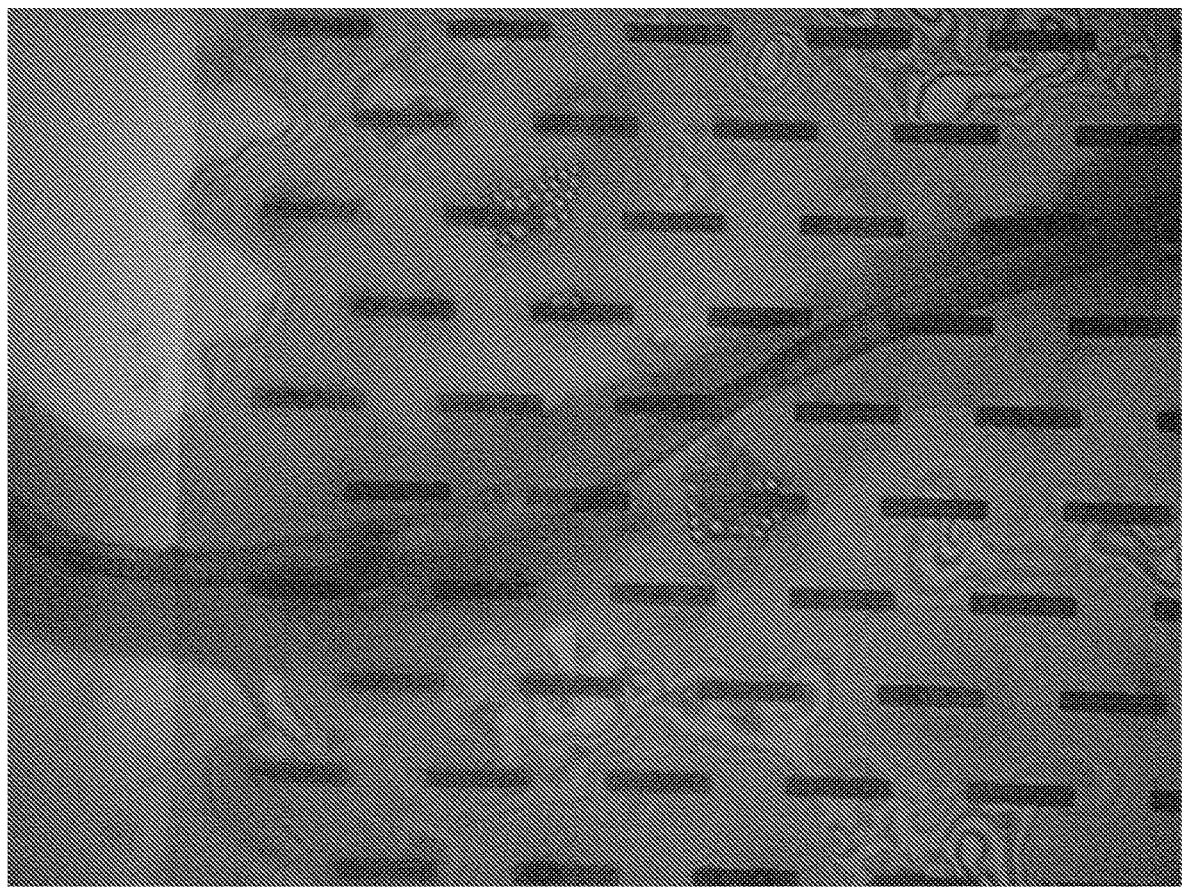
FIG. 7 shows a second example of an aggregation experiment. (A) shows the microslit filter before the filtration step and (B) shows the microslit filter after the filtration step.
Figure 8:
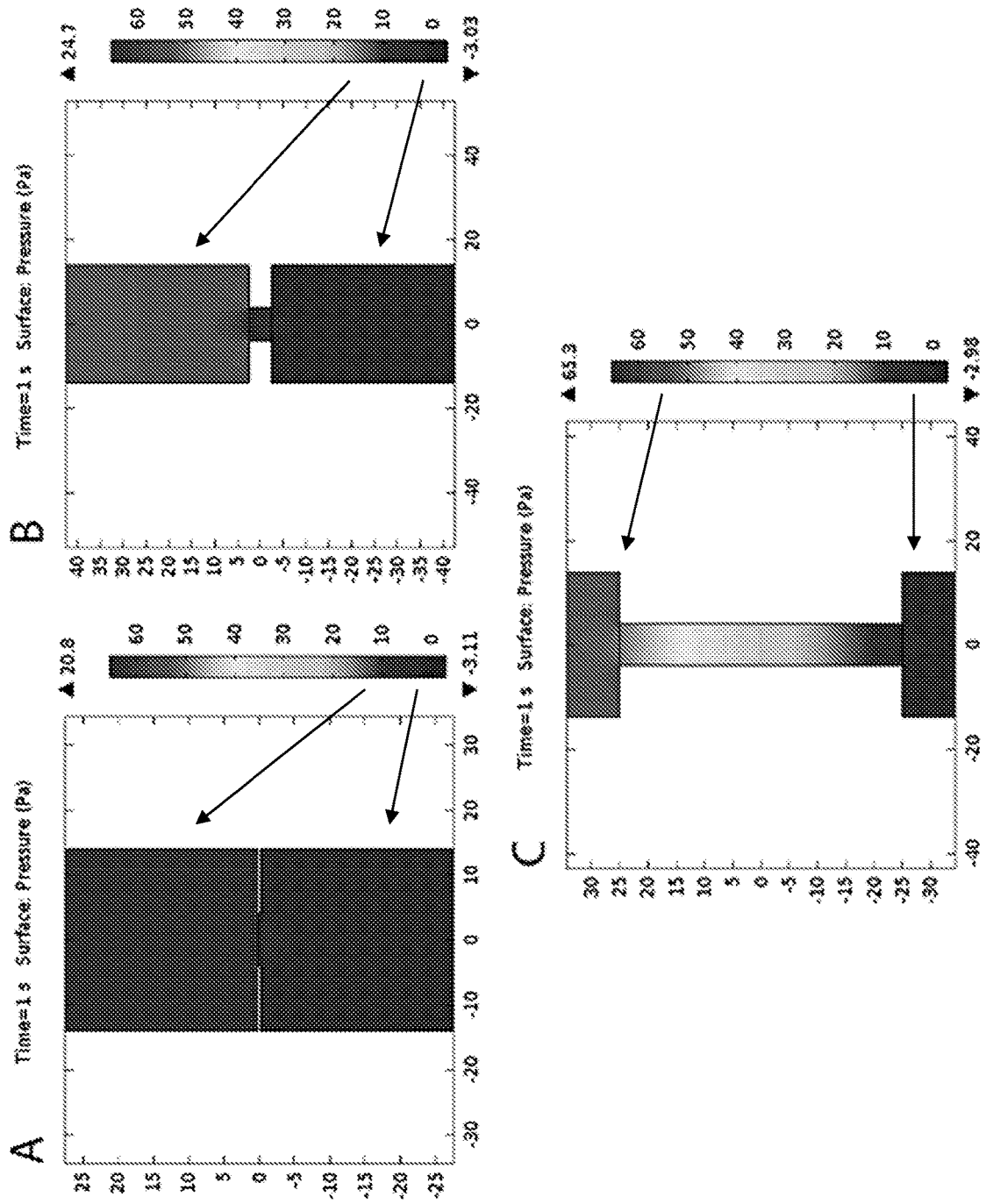
FIG. 8 provides a diagram demonstrating the shear stress profile for a representative microslit filter as a function of pressurization. Pressure drop through pores of various lengths for a constant inlet velocity (flow rate). (A) A 400 nm tall pore has a pressure drop of 20.8 Pa. (B) A 5 μm tall pore has a pressure drop of 25 Pa. (C) A 50 μm tall pore has a pressure drop of 65 Pa. The higher the pressure drop, the higher the shear experienced by the cells as they travel through the pore.

FIG. 7 shows a second example of an aggregation experiment. One-half (0.5) mL of human whole blood from an adult donor was combined with sodium heparin (2.5% final concentration) and 6.7×10$^4$ 6-8 μm diameter polystyrene beads coated with goat polyclonal anti-human IgG antibody, and incubated for 20 minutes at room temperature. Following the incubation, the mixture was filtered by hydrostatic pressure-driven filtration through microslit filters with 9×50 μm openings, three 0.7×3 mm membranes of 400 nm thick silicon nitride on 5.4×5.4 mm, 0.3 mm thick silicon substrates. The microslit filters were imaged by light microscopy after the filtration step. FIG. 7A shows the microslit filter before the filtration step, while FIG. 7B shows the microslit filter after the filtration step. The range of human blood IgG content for adults is 70-160 mg/mL (Vadd and Staros, 2013). This incubated mixture comprised approximately 1.3×10$^{17}$ to 3.0×10$^{17}$ IgG molecules and 6.8×10$^4$ beads, wherein the beads had a molecular binding capacity of 500,000 IgG molecules/bead. Thus the IgG-to-molecular binding capacity ratio was approximately 3.8×10$^6$:1 to 8.8×10$^6$:1.

EXAMPLE 4

This example provides a description of examples of a method of the present disclosure.

Figure 9:
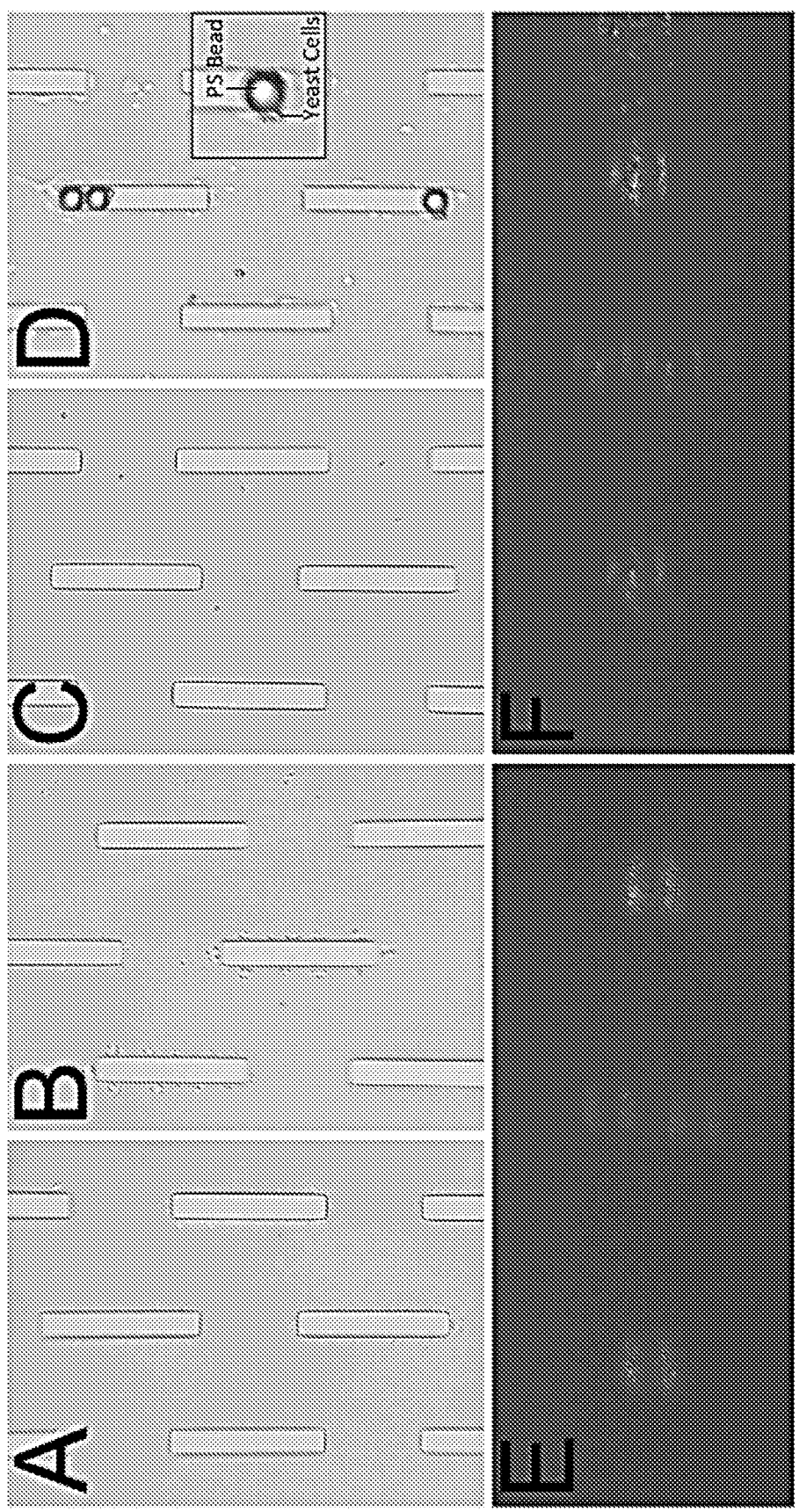
FIG. 9 provides a further exemplary use of microslit filters, capture particles and binding agents, for capturing and detecting a biological species. Specific detection of cell surface streptavidin-expressing S. cerevisiae via biotinylated bead (6 μm) complex formation and retention by nanomembranes. A), S. cerevisiae alone (B), and wild-type S. cerevisiae pre-mixed with beads (C) demonstrates no retention on membrane. As anticipated the corresponding diffraction pattern remains consistent for non-fouled microslits (example in (E)). However, surface Streptavidin-producing S. cerevisiae pre-mixed with biotinylated beads is easily retained ((D), annotation in subframe). This partial slit occlusion induces a clear diffraction pattern shift evident for bead-captured S. cerevisiae (F) relative to wild-type control.

FIG. 9 demonstrates capture and detection of a particular cell type and its detection by the direct assay method of the present disclosure. Either wild-type or streptavidin-cell surface expressing Saccharomyces cervisiae were mixed with biotinylated 6 μm diameter polystyrene beads and incubated to form potential complexes. Solution samples were subsequently filtered by mild vacuum pressure through microslit filters similar to those shown in FIG. 7. In this example, solutions of beads alone (A), S. cerevisiae alone (B), and wild-type S. cerevisiae pre-mixed with beads (C) demonstrated no retention by the microslit filter. No observable differences in the resulting diffraction patterns were recorded following filtration; i.e., the reference microslit filter diffraction pattern shown in (E) had no observable differences. Only S. cerevisiae expressing streptavidin on their cell surfaces resulting in retention and diffraction pattern shift ((D), annotation in subframe). Partial slit occlusion induced a diffraction pattern shift for biotinylated bead-captured S. cerevisiae (F) relative to wild-type control cells.

EXAMPLE 5

This example provides a description of an exemplary fluidic device and method for its use of the present disclosure.

Figure 10:
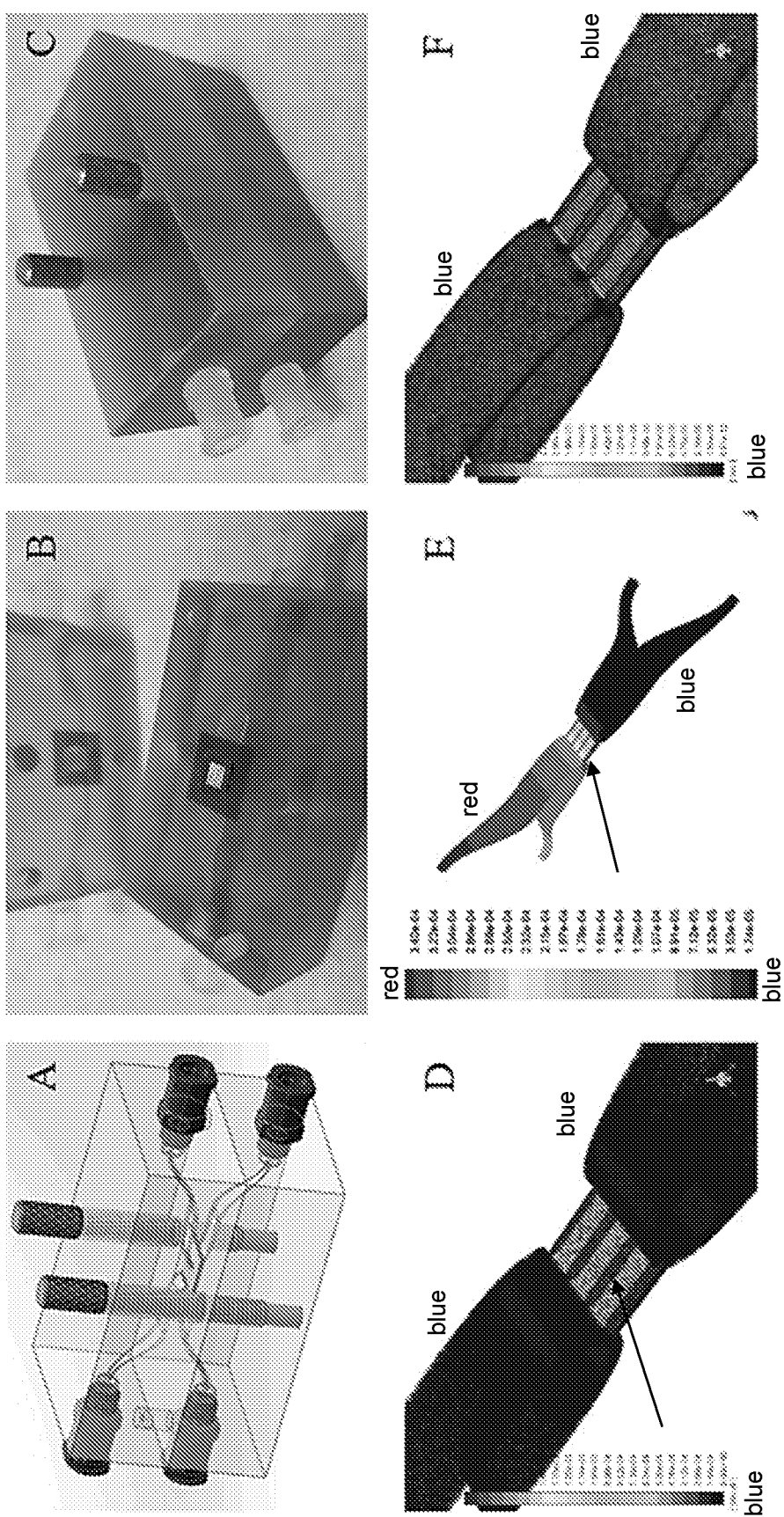
FIG. 10 provides an exemplary tangential fluidic device for incorporating microslit filters. Prototype Fluidic Module with polycarbonate body and elastomeric gaskets fabricated by 3D-printing. CAD modeling software was used to render a prototype device (A) suitable for polyjet multi-material printing (B-C). Comoutational Fluid Dyanmics analysis was performed on the design to verify surface velocities (D), system pressure (E) and sheer stress (F) would not impact studies performed using a variety of sample types ranging from whole blood to cell suspensions. Photos of the first-generation print and its related schematics are shown for the two-piece, clam shell design. The elastomer provides a sealing surface for nanomembrane chips. The sample preparation and affinity capture modules will be similarly designed and printed.

FIG. 10 shows a tangential flow-based fluidic device for incorporating microslit filters. A prototype Fluidic Module with polycarbonate fluidic channels in the body and elastomeric gaskets for microslit filter integration was fabricated by 3D-printing. CAD modeling software was used to render a prototype device (A) suitable for multi-material 3D-printing (B-C). Computational fluid dynamics analysis was performed on the design to verify surface velocities (D), system pressure (E) and sheer stress (F) to ensure such exemplary prototypes would be suitable fluidic devices for the methods of the present disclosure.

EXAMPLE 6

This example provides a description of devices and methods of the present disclosure.

Figure 11:
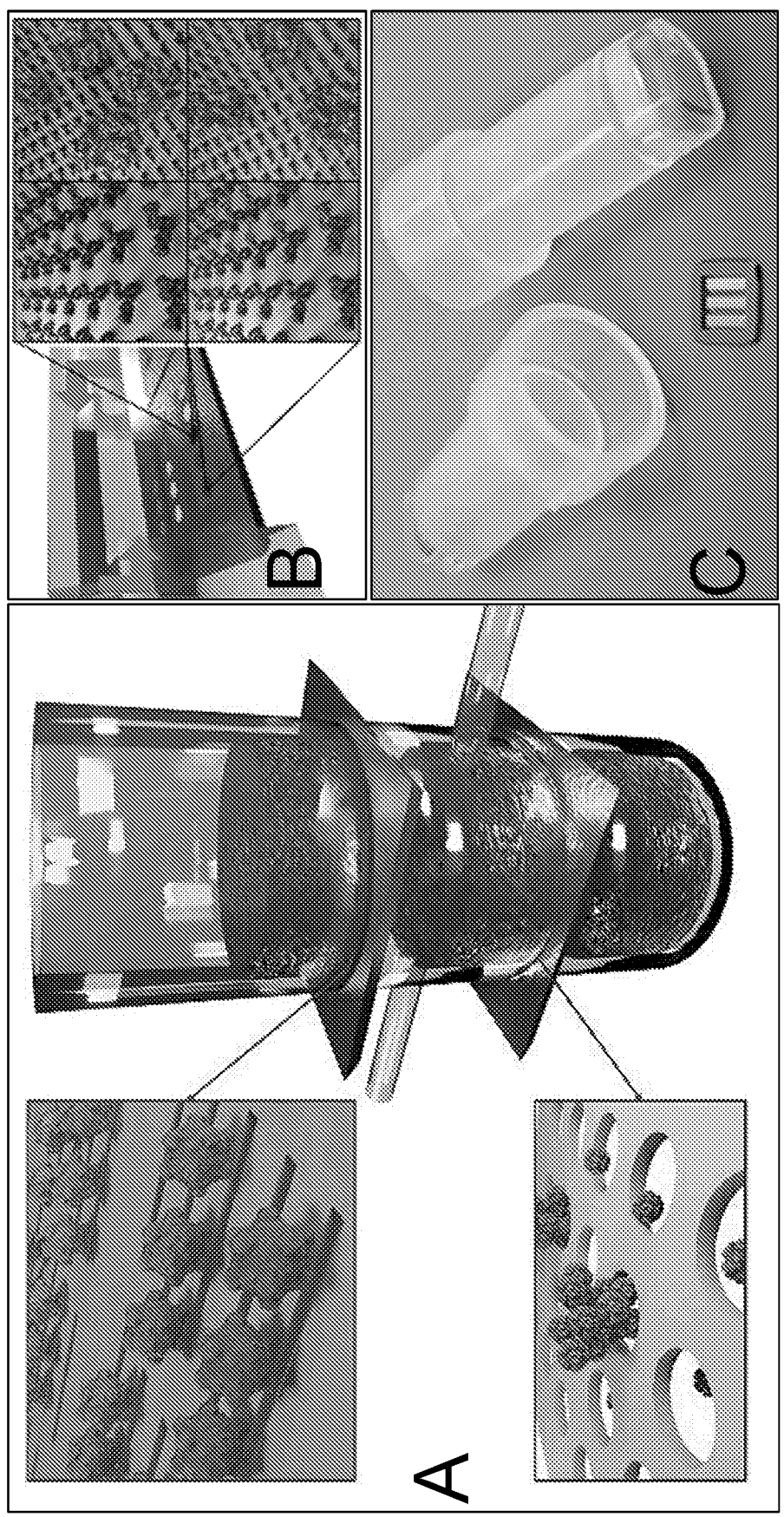
FIG. 11 provides an exemplary use of microslit filters and sorting membranes in a fluidic device for a sample preparation and an analytical assay. Membrane technologies enable a single device for multi-analyte detection of exosomes via liquid biopsy. (A) A device concept utilizing multi-membrane stack-well design where a urine sample is initially removed of cells through a pre-filter (well 1), then exosome complexes are formed and retained on a secondary membrane (Well 2) soluble proteins and other interferants are washed through the membrane into a waste cell (well 3). (B) Exosomes are then probed via membrane-bound sandwich fluorescent immunoassay arrays. (C) A standard SepCon membrane device (and unassembled membrane) affording a low-volume sample cup and variable membrane size which will enable the proof of concept work proposed in this project.

FIG. 11 depicts an exemplary fluidic device for carrying out methods of an upstream sample preparation and an analytical assay. (A) A fluidic device concept utilizing multiple microslit filter and sorting membrane elements in successive (i.e., different fluidic) planes, wherein an upstream sample preparation step removes cells and protein aggregates from a biofluid (e.g., urine) in a first fluidic chamber (e.g., well 1), then analyte-capture complexes are formed in a second fluidic chamber (e.g., well 2). In this example, the analytes of interest are extracellular vesicles (e.g., exosomes) and the captured exosomes are retained by a sorting membrane (e.g., nanoporous silicon nitride, NPN). Soluble proteins and other interferents are washed through the membrane into a waste cell (well 3). (B) The analyte of interest (e.g., exosomes) is then interrogated by an analytical method. In this example a membrane-bound sandwich fluorescent immunoassay array is used as the analytical method.

EXAMPLE 7

This example provides a description of examples of the methods of the present disclosure.

FIGS. 12-18 demonstrate examples of methods for an upstream sample preparation and an analytical assay.

Figure 12:
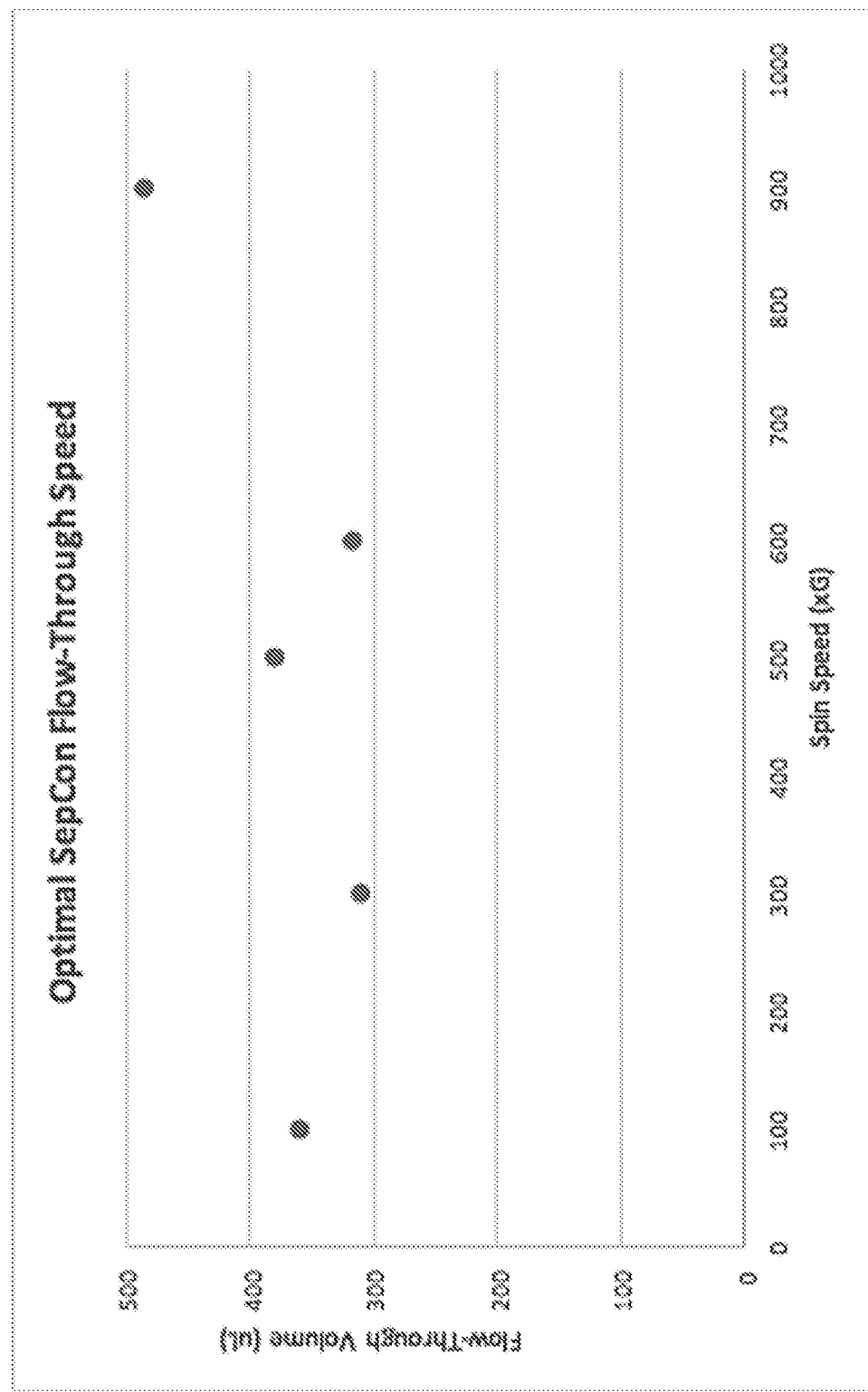
FIG. 12 demonstrates an upstream sample preparation for a representative biofluid. The figure shows urine flow through volumes at different spin speeds. 500 µL SepCon volume, duration of spin=5 minutes.

FIG. 12 demonstrates an upstream sample preparation for a representative biofluid. One half (0.5) mL of human urine was filtered through fluidic devices similar to those shown in FIG. 1A. The fluidic devices incorporated microslit filters, wherein the urine was filtered by centrifuge-driven filtration through microslit filters with 1×50 µm openings, three 0.7×3 mm membranes of 400 nm thick silicon nitride on 5.4×5.4 mm, 0.3 mm thick silicon substrates. The centrifugation was carried out for 5 minutes at a range of relative centrifugal forces and the volume of urine that permeated the microslit filter (i.e., the flow-through volume) was recorded and is presented as a function of relative centrifugal force.

Figure 13:
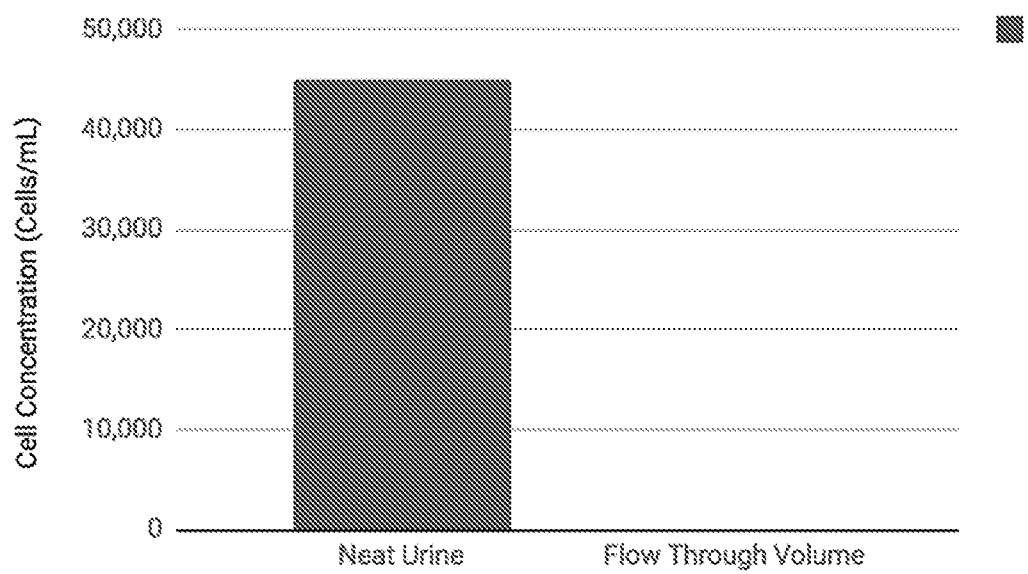
FIG. 13 reports the removal of cells in the urine samples during the microslit filtration step as similarly performed in FIG. 12; however, in this example, the centrifugation was performed at one relative centrifugal force. One half (0.5) mL of urine was filtered through the same fluidic devices and microslit filters as used in FIG. 12.

FIG. 13 reports the removal of cells in the urine samples during the microslit filtration step as similarly performed in FIG. 12; however, in this example, the centrifugation was performed at one relative centrifugal force. One half (0.5) mL of urine was filtered through the same fluidic devices and microslit filters as used in FIG. 12. The centrifugation was performed at 900×G for 5 minutes. The cells in the input urine sample and flow-through volume were counted manually using a hemocytometer and Trypan blue staining. To determine the number of cells in the starting urine sample, 1 mL was centrifuged without any filtration and the cells resuspended in 100 µL of phosphate-buffered saline (PBS) before Trypan blue staining and counting.

Figure 14:
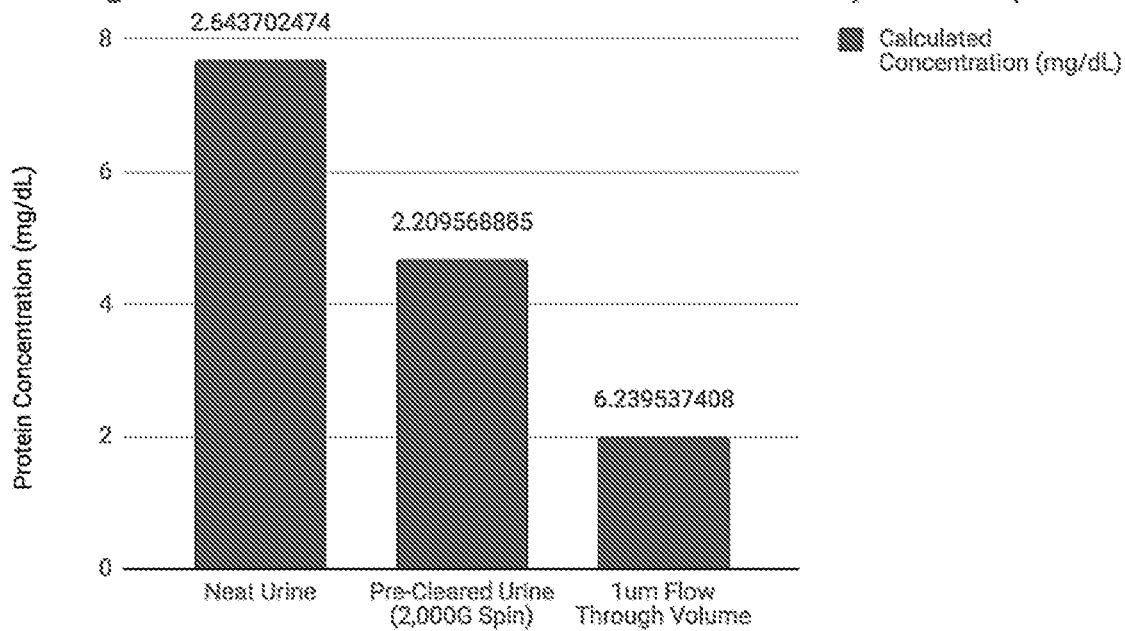
FIG. 14 reports the removal of matrix proteins from urine samples during the microslit filtration step as similarly performed in FIG. 13. The data is from a Bradford assay assessing total protein concentration. The volume used was ~500 µL, 1 µm chips filter 75% of protein from the neat urine. Centrifugation (2 kG spins) is used to pellet and removes 50% of protein from neat urine. Note: possible bacterial contamination. CV % are above bars.

FIG. 14 reports the removal of matrix proteins from urine samples during the microslit filtration step as similarly performed in FIG. 13. One half (0.5) mL of urine was filtered through the same fluidic devices and microslit filters as used in FIG. 13. The protein concentration was measured by the Bradford method, well-known to those skilled in the art. The centrifugation was performed at 900×G for 5 minutes. The protein concentration of the resulting flow-through volume was compared to that of the input urine sample as-is (i.e., neat urine) and to a supernatant from a 2,000×G centrifugation for 30 minutes at 4° C. of the input urine sample without any filtration (i.e., pre-cleared urine). A 25 µL aliquot of the three samples (input urine, pre-cleared urine, and flow-through volume) was analyzed by the Bradford method for total protein concentration. A standard curve using bovine serum albumin (BSA; Sigma-Aldrich Corp.) was used as a reference series to determine protein concentration. PBS was used as a blank and as a dilutant for the protein standards. Samples were loaded into a 96-well plate for absorbance readings at 595 nm wavelength on a SpectraMax i3 plate reader. A 100 µl aliquot of Bradford reagent was incubated with each sample well at room temperature for 20 minutes prior to reading.

Figure 15:
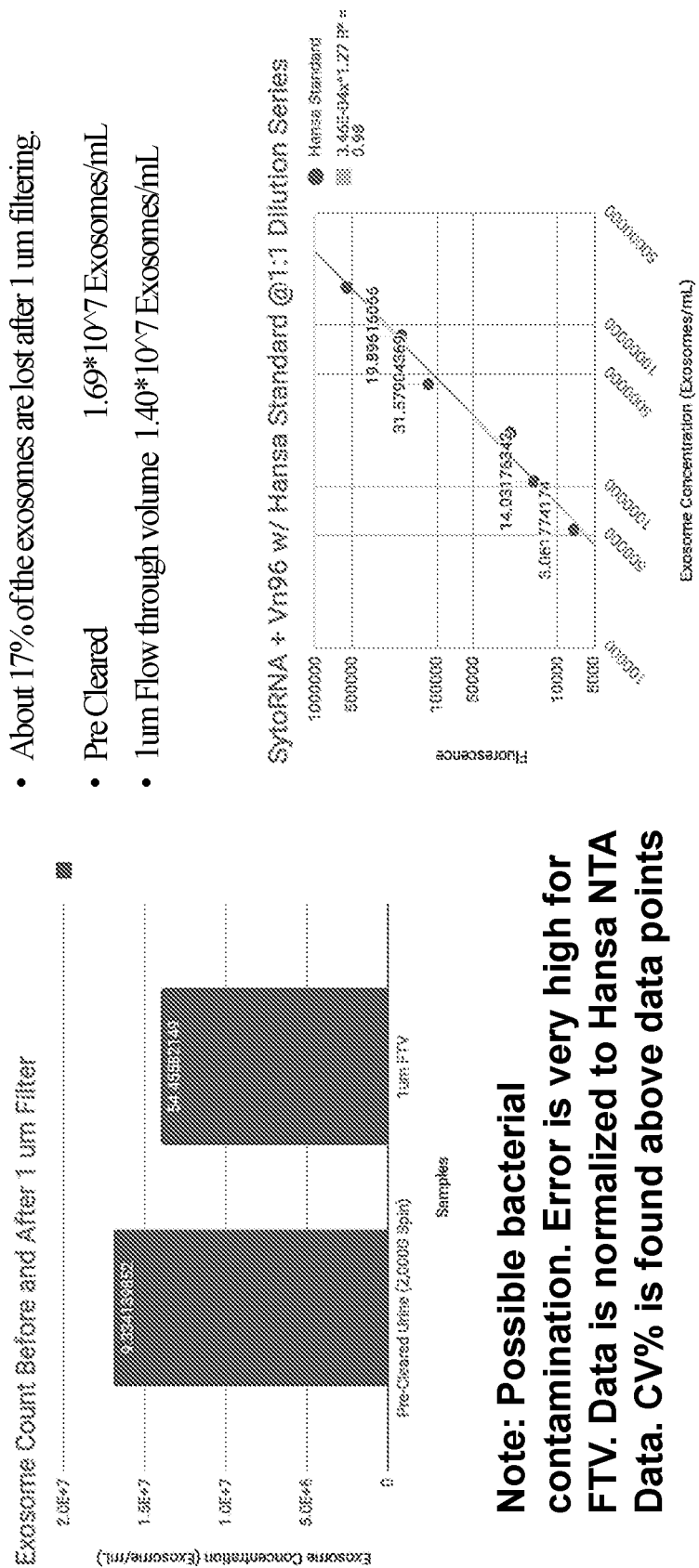
FIG. 15 reports the loss of an example analyte of interest during the microslit filtration step as similarly performed in FIG. 13. The figure shows the exosome loss due to 1 µm Microslit.

FIG. 15 reports the loss of an example analyte of interest during the microslit filtration step as similarly performed in FIG. 13. In this example, the analyte of interest is an extracellular vesicle (e.g., exosome) found in urine. One half (0.5) mL of urine was filtered through the same fluidic devices and microslit filters as used in FIG. 13. The centrifugation was performed at 900×G for 5 minutes and the resulting flow-through volume (i.e., FTV) was assessed for exosome concentration. Exosome concentration was also assessed in the supernatant from a 2,000×G centrifugation for 30 minutes at 4° C. of the input urine sample without any filtration (i.e., pre-cleared urine). A reference standard was created by first re-suspending lyophilized exosomes (Hansa Corp.) to a final concentration of $10^9$ exosomes/mL in PBS. This concentration was confirmed by nanoparticle tracking analysis on a Malvern Nano Sight NS300 particle counting instrument. The dilution series of exosome reference standards was diluted in PBS. The FTV, pre-cleared urine, and the reference standards were incubated with 5 µm RNASelect® dye (Thermo Fisher Inc.) for 20 minutes at 37° C. so that the RNA within these exosomes was fluorescently labeled. Next, VN96 peptide (New England Peptide Inc.) was added to a final concentration of 90-100 µg/mL and incubated for 30 minutes at room temperature. The VN96-exosome complexes were then pelleted by centrifugation at 5,000×G for 5 minutes. The pellets were washed twice in 1 mL PBS with repeated centrifugation and the final pellet was dissolved by repeated pipetting in 400 µL of 2 M NaCl and left at 4° C. overnight. The samples were transferred to 96-well plates and the fluorescence of all samples was measured at 490 nm emission and 530 nm excitation using a SpectraMax i3 plate reader.

Figure 16:
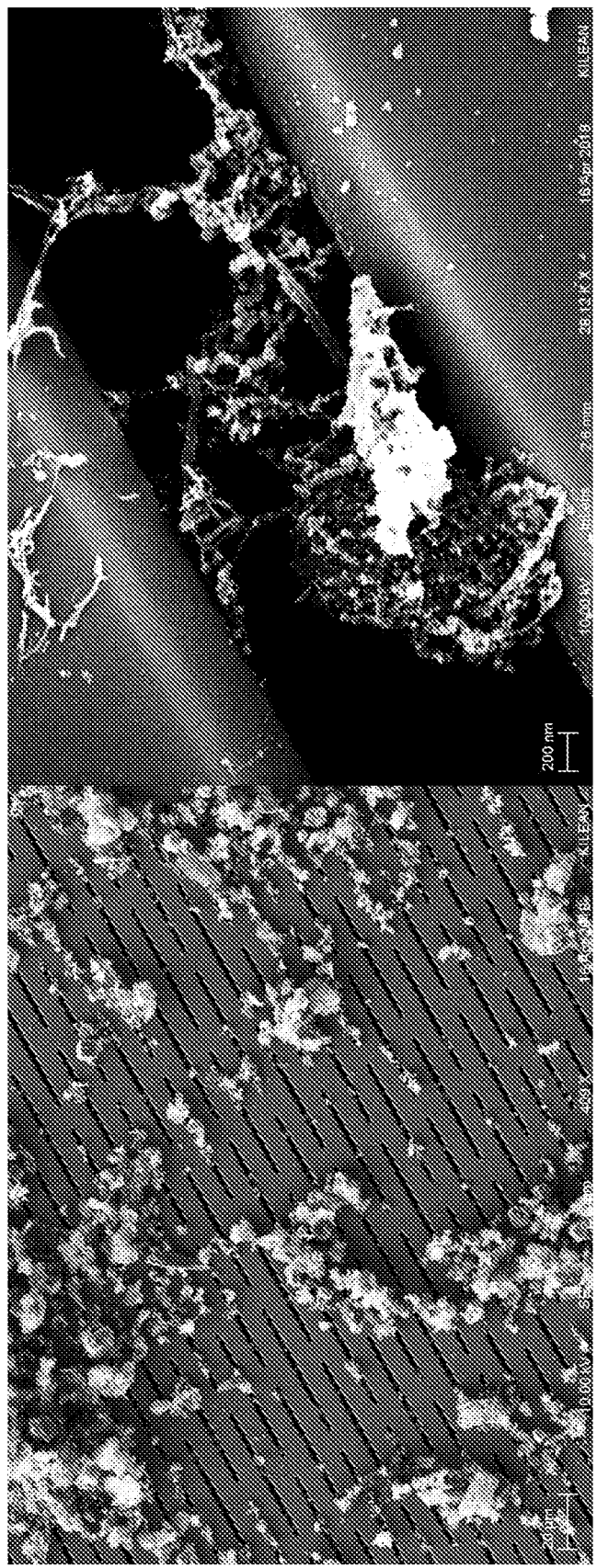
FIG. 16 demonstrates the resulting microslit filter surface after the microslit filtration step as similarly performed in FIG. 13. The figure shows electron microscopy of a 1 µm slit after filtering urine. Left shows an image showing protein, salts, and cells on the surface of a 1 µm slit. Right shows an image showing what is believed to be Tamm-Horsfall protein (THP) and substances sticking to their surface.

FIG. 16 demonstrates the resulting microslit filter surface after the microslit filtration step as similarly performed in FIG. 13. In this example, the retention of cells and matrix proteins are shown, presumably urothelial cells and Tamm-Horsfall protein filaments, respectively. Samples were fixed with 25 µL of 2.5% glutaraldehyde for ten minutes by adding the fixative to the fluidic devices. The microslit filters were then extracted from the fluidic devices and transferred to 6-well plates with 50% ethanol. The samples were dehydrated in sequential ethanol steps (10% increase per step) to 100% ethanol. The samples were then dried using a Samdri®-PVT-3D critical point dryer (tousimis Inc.) and then sputter-coated with 10 nm of gold in a Denton PVD system (Denton Vacuum Corp.). Samples were then imaged in a Zeiss Auriga (Carl Zeiss Microscopy GmbH) field emission scanning electron microscope with a 10 kV accelerating voltage.

Figure 17:
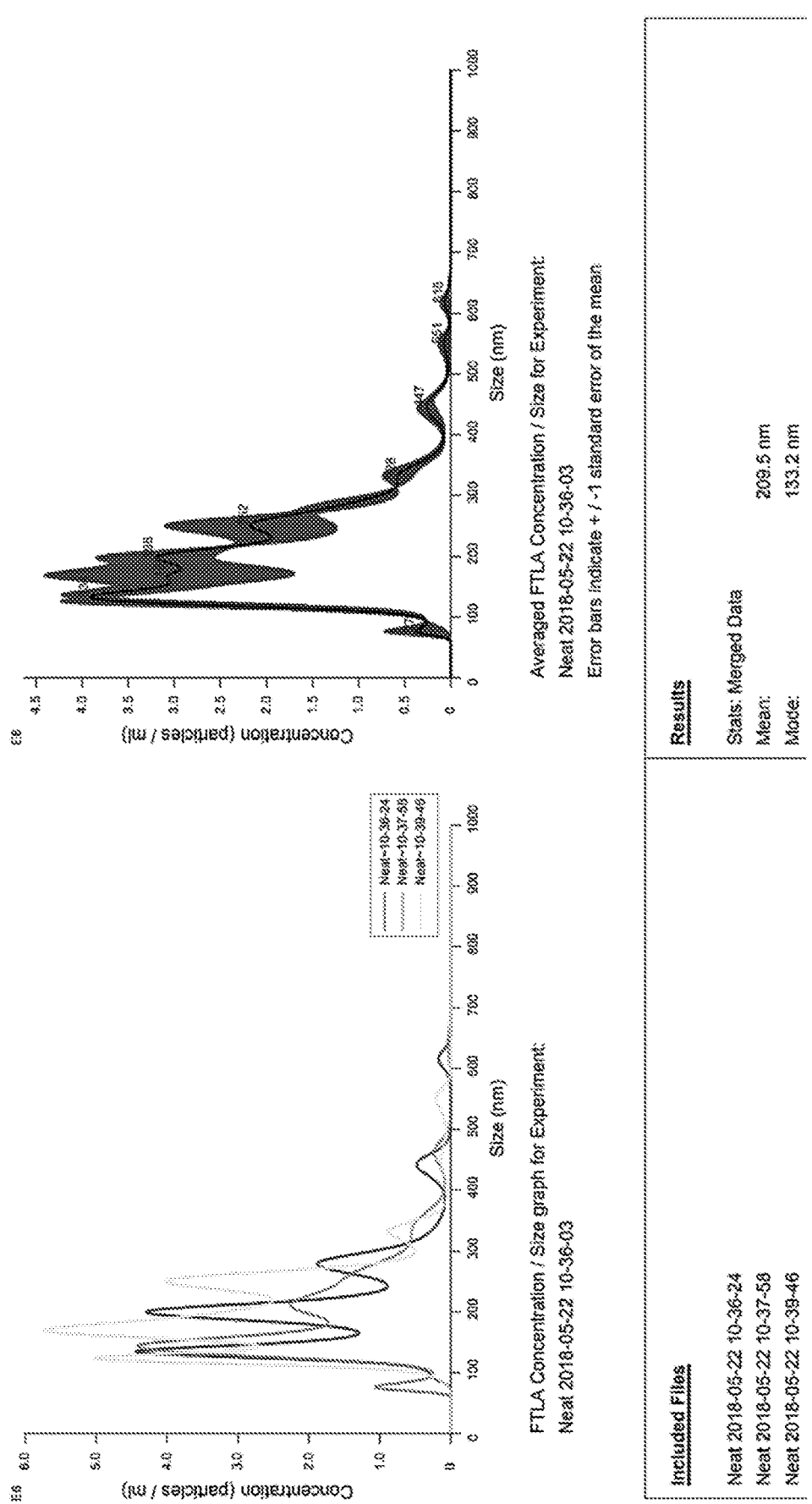
FIG. 17 demonstrates a comparison between the number of exosomes in an input urine sample to that in the flow-through volume following the microslit filtration step as similarly performed in FIG. 13. In this example, the number of exosomes in the approximate 100 nm diameter size range was determined by nanoparticle tracking analysis using a Malvern NS300 particle counter.
Figure 17:
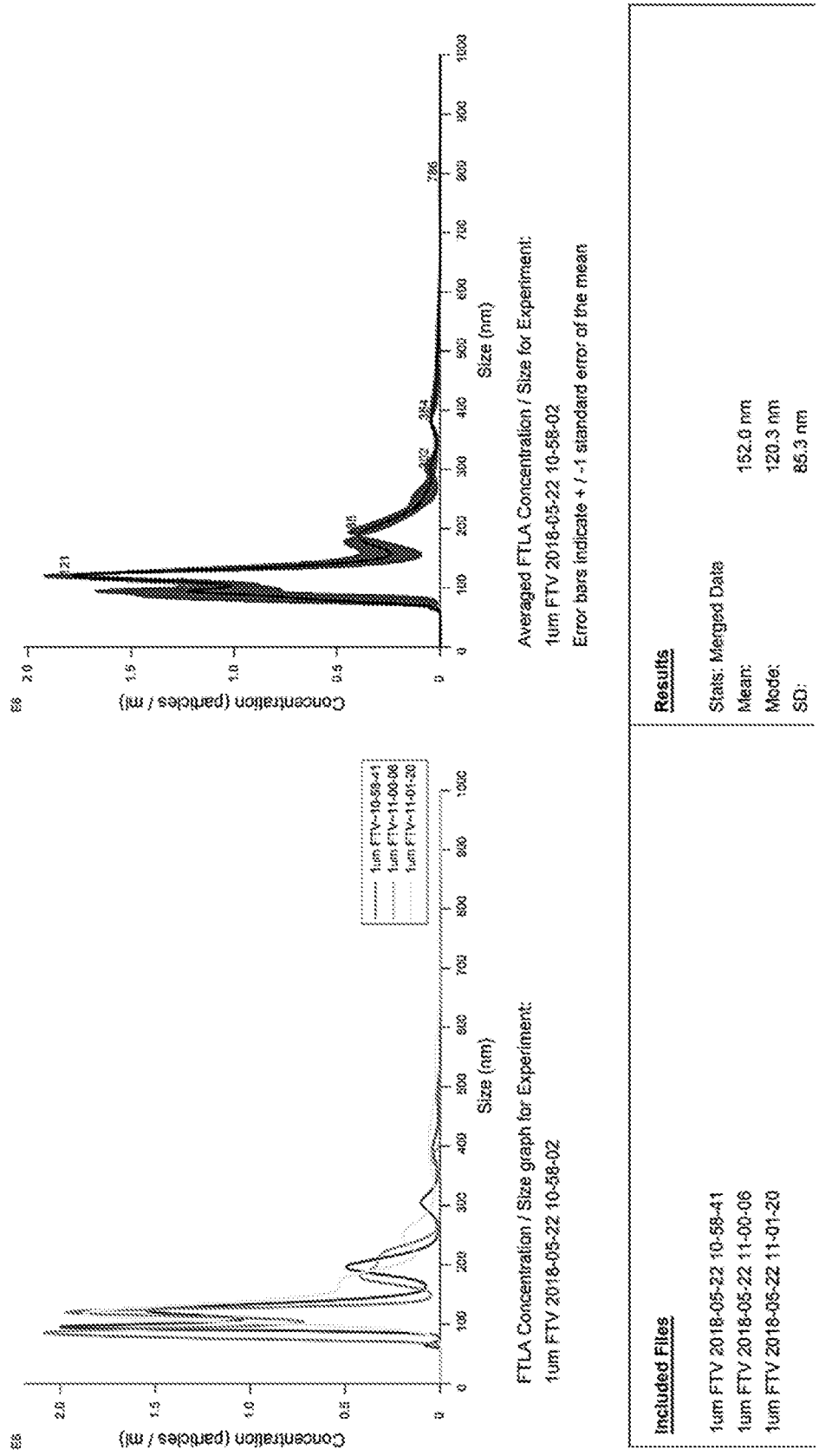

FIG. 17 demonstrates a comparison between the number of exosomes in an input urine sample to that in the flow-through volume following the microslit filtration step as similarly performed in FIG. 13. In this example, the number of exosomes in the approximate 100 nm diameter size range was determined by nanoparticle tracking analysis using a Malvern NS300 particle counter.

Figure 18:
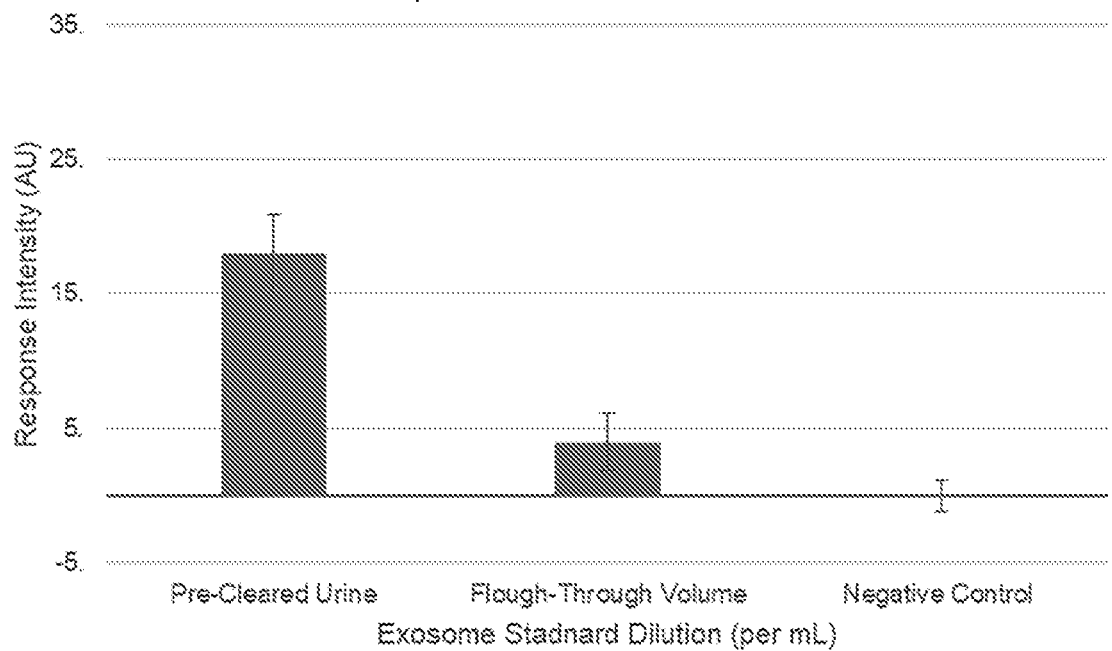
FIG. 18 demonstrates the results of an upstream sample preparation and subsequent capture of an analyte of interest on an exemplary sorting membrane, as well as an exemplary analytical assay to assess the analyte. The figure shows CD63 response. Microslit membranes of the present disclosure are able to pass exosomes during fractionation of urine samples, while nanoporous membranes are able to capture exosomes from the resultant flow-through. 0.5 mL urine was fractionated as in FIG. 3 and the input urine and the flow-through fraction were analyzed for the presence of the exosomal marker CD63 by anti-CD63 antibody dot-blot. Similar microslit-treated fractions were prepared and spun against a nanoporous mem-brane (50 nm average pores). Input sample and flow-through from the nanoporous-treated samples were analyzed by anti-CD63 dot-blot. Note the presence of CD63 in initial urine and microslit flow-through, but is substantially decreased in nanoporous flow-through fractions and absent in the control. All dot-blots were run against a dilution series of pre-purified, commercially sourced urinary exosomes (Hansa) as a reference.

FIG. 18 demonstrates the results of an upstream sample preparation and subsequent capture of an analyte of interest on an exemplary sorting membrane, as well as an exemplary analytical assay to assess the analyte. One half (0.5) mL of urine was filtered through the same fluidic devices and microslit filters as used in FIG. 13. The centrifugation was performed at 900×G for 5 minutes. The input urine and the flow-through volume were analyzed for the presence of the exosomal marker CD63 by anti-CD63 antibody dot-blot. The flow-through volume was then centrifuged in a fluidic device similar to that shown in FIG. 1A, wherein this fluidic device incorporated a sorting membrane comprising nanoporous silicon nitride (NPN) with 50 nm average pore diameter, approximately 15% porosity, and four 0.3×3 mm, 100 nm thick membranes on 5.4×5.4 mm, 0.3 mm thick silicon substrates. The centrifugation with the sorting membrane was performed at 600×G for 5 minutes. The flow-through volume from the sorting membrane fluidic device centrifugation was similarly analyzed for the presence of the exosomal marker CD63 by anti-CD63 antibody dot-blot. Dot-blots were performed by spotting 2 µL of sample onto nitrocellulose membranes (previously washed and dried). Control spots included 0.1% BSA, buffer alone (Tris-buffered saline, TBS), TBS with 0.1% Tween 20 (TBS-T, and anti-CD63 antibody (1 µg/mL solution), and avidin-alkaline phosphatase (1 ng/mL solution). Membranes were allowed to dry after spotting and then blocked in blocking solution (0.1% BSA in TBS-T) for 30 minutes and then washed. Membranes were incubated with biotinylated antibody (1 µg/mL anti-CD63 IgG; Bio Legend Corp.) for 60 minutes. Membranes were washed, incubated with avidin-alkaline phosphatase (1 ng/mL; Thermo Fisher Inc.) for 30 minutes, and then washed. Membranes were then incubated with the One-step NBT/BCIP reagent solution (Thermo Fisher Inc.) and stopped with deionized water when the desired spot intensity was reached. Blots were then scanned by a flatbed scanner on a Brother printer/scanner. Images were then gray-scaled and inverted in NIH Image J software for spot intensity. Spots were measured for mean, median, area of intensity, and standard deviation. The spot intensity of the 0.1% BSA sample was subtracted from sample values as a reference and intensities were then compared to each other. A dilution series of pre-purified exosomes (Hansa Corp.) was used as a reference standard series for relative quantization.

NON-PATENT CITATIONS

1. Loken, M. R., Shah, V. O., Dattilio, K. L. & Civin, C. I. Flow cytometric analysis of human bone marrow: I. Normal erythroid development. Blood 69, 255-263 (1987).
2. Leverett, L. B., Hellums, J. D., Alfrey, C. P. & Lynch, E. C. Red blood cell damage by shear stress. Biophys J 12, 257-273, doi:10.1016/s0006-3495(72)86085-5 (1972).
3. Tian, H., Hümer, A. F. & Landers, J. P. Evaluation of silica resins for direct and efficient extraction of DNA from complex biological matrices in a miniaturized format. Analytical biochemistry 283, 175-191 (2000).
4. Vadde, R., and Staros, E. B. Immunoglobulins: Reference Range, Interpretation, Collection and Panels (Updated 1 Jul. 2013). http://emedicine.medscape.com/article/2157901-overview; accessed 15 Feb. 2017.

130. PATENT CITATIONS

1. Huff, J. B. et al. Devices and methods for sample analysis. WO2016161402A1.
2. Miller, B. and Rothberg, L. Method for biomolecular sensing and system thereof. U.S. Pat. No. 7,292,349.
3. Sitdikov, R. A., et al. Target Capture System. U.S. Ser. No. 14/107,315.
4. Shestopalov, A., McGrath, J. & Li, X. Methods for depositing a monolayer on a substrate. U.S. Pat. No. 9,089,819.
5. Striemer, C. C., et al. Nanoporous Silicon Nitride Membranes, and Methods for Making and Using Such Membranes. U.S. Pat. No. 9,789,239.

Although the present disclosure has been described with respect to one or more particular embodiments and/or examples, it will be understood that other embodiments and/or examples of the present disclosure may be made without departing from the scope of the present disclosure.

The invention claimed is:

1. A device comprising:
 a microslit filter defining a plurality of openings;
 wherein the microslit filter has a thickness from 50 nm to 25 µm;
 a porosity from 1% to 75% and
 wherein the openings are cubic prisms or trapezoids;
 the openings have a width from 0.5 µm to 15 µm and a length from 5 µm to 100 µm; and
 the openings have an aspect ratio (width:length) from 1:0.33 to 1:200.

2. The device of claim 1, further comprising a first fluidic channel or chamber on a side of the microslit filter and a second fluidic channel or chamber on an opposite side of the microslit filter.

3. The device of claim 1, wherein the microslit filter is 400 nm thick and has 17% porosity, wherein the openings are 9 µm in width and 50 µm in length, and wherein the openings have an aspect ratio of 1:5.5; or
 wherein the microslit filter is 400 nm thick and has 17% porosity, wherein the openings are 8 µm in width and 50 µm in length, and wherein the openings have an aspect ratio of 1:6.25.

4. The device of claim 1, further comprising at least two sorting membrane elements.

5. The device of claim 1, further comprising a transducer for mechanical sonication, a heating element, and/or UV light source.

6. The device of claim 1, wherein the microslit filter are functionalized to decrease adhesion of biofluid constituents; or
 wherein the microslit filter and/or sorting membranes are functionalized to increase interactions between retained complexes and the microslit filter and/or sorting membranes.

7. The device of claim 1, comprising a light source and a detector configured to record optical signals of an assay.

8. A method comprising:
 forming analyte-affinity moiety-capture particle complexes with an analyte in a sample;
 filtering the sample, thereby isolating at least a portion of the analyte-affinity moiety-capture particle complexes wherein the filtering uses a microslit filter of claim 1; and
 optionally, eluting the isolated analyte-affinity moiety-capture particle complexes and/or disassociating the isolated retained analyte-affinity moiety-capture particle complexes to liberate the analyte from the analyte-affinity moiety-capture particle.

9. The method of claim 8, further comprising performing at least one analytical assay on the isolated analyte-affinity moiety-capture particle complexes and/or the liberated analyte.

10. The method of claim 8, wherein the analyte is one of intact cells, sub cellular components, proteins, nucleic acids, carbohydrates, lipids, peptides, viruses, bacteria, fungi, drugs, metabolites, low molecular mass species, or a combination thereof.

11. The method of claim 8, wherein the biofluid is one of cell lysates, venous whole blood, arterial whole blood, plasma, serum, sputum, urine, cerebrospinal fluid, or conditioned cell culture media.

12. The method of claim 8, wherein the capture agent is an organic material, an inorganic material, or a combined organic-inorganic material.

13. The method of claim 8, wherein the filtering includes one of gravity flow, hydrostatic pressure, pumping, vacuum, centrifugation, gas pressurization, or tangential flow and/or the filtering occurs at a pressure from 10 Pa to 1.0 kPa.

14. The method of claim 8, wherein the capture particles have a diameter less than a width of the microslit filter.

15. The method of claim 8, wherein the capture particles have a diameter greater than a width of the microslit filter.

16. A method comprising:
  binding a first ligand on an analyte in a biofluid using a first binding agent, thereby forming an analyte-first binding agent complex;
  adding capture particles to the biofluid, wherein the first binding agent is bound by the capture particles, thereby forming an analyte-first binding agent-capture particle complex;
  filtering the biofluid having the analyte-first binding agent-capture particle complex with a microslit filter of claim 1; and
  optionally, eluting or disassociating any of the analyte-first binding agent-capture particle complex that is retained by the microslit filter.

17. The method of claim 16, further comprising performing at least one analytical assay on a analyte of the analyte-first binding agent-capture particle complex.

18. The method of claim 16, wherein the analyte is one of intact cells, sub cellular components, proteins, nucleic acids, carbohydrates, lipids, peptides, viruses, bacteria, fungi, drugs, metabolites, or a combination thereof.

19. The method of claim 16, wherein the biofluid is one of cell lysates, venous whole blood, arterial whole blood, plasma, serum, sputum, urine, cerebrospinal fluid, or conditioned cell culture media.

20. The method of claim 16, wherein the first binding agent is one of monoclonal antibodies, polyclonal antibodies, fragments of monoclonal antibodies, fragments of polyclonal antibodies, DNA aptamers, RNA aptamers, peptides, modified peptide derivatives, lectins, bacteriophages, small molecules, or proteins, or a combination thereof; and
  wherein the first binding agent is monovalent or multivalent.

21. The method of claim 16, further comprising adding a second binding agent to the biofluid, wherein the second binding agent captures the first binding agent.

22. The method of claim 16, wherein the capture agent is an organic material, an inorganic material, or a combined organic-inorganic material.

23. The method of claim 16, wherein the filtering includes one of gravity flow, hydrostatic pressure, pumping, vacuum, centrifugation, gas pressurization, or tangential flow and/or the filtering occurs at a pressure from 10 Pa to 1.0 kPa.

24. The method of claim 16, wherein the first binding agent includes two different types of the first binding agent, and wherein the capture particles include two different types of the capture particles.

25. The method of claim 16, wherein the capture particles have a diameter less than a width of the microslit filter.

26. The method of claim 16, wherein the capture particles have a diameter greater than a width of the microslit filter.

* * * * *